(12) United States Patent
Inoue et al.

(10) Patent No.: US 9,250,552 B2
(45) Date of Patent: Feb. 2, 2016

(54) POLYMERIZABLE MONOMER, POLYMERIC COMPOUND, CHARGE CONTROL AGENT CONTAINING THE POLYMERIC COMPOUND, AND DEVELOPER BEARING MEMBER AND TONER WHICH CONTAIN THE CHARGE CONTROL AGENT

(75) Inventors: Kei Inoue, Yokohama (JP); Yasuaki Murai, Kawasaki (JP); Ryuji Murayama, Yokohama (JP); Kazuyuki Sato, Kawasaki (JP); Soichiro Kawakami, Machida (JP); Masashi Hirose, Machida (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 61 days.

(21) Appl. No.: 14/006,407

(22) PCT Filed: Mar. 27, 2012

(86) PCT No.: PCT/JP2012/058792
§ 371 (c)(1),
(2), (4) Date: Sep. 20, 2013

(87) PCT Pub. No.: WO2012/133881
PCT Pub. Date: Oct. 4, 2012

(65) Prior Publication Data
US 2014/0011130 A1    Jan. 9, 2014

(30) Foreign Application Priority Data

Mar. 30, 2011  (JP) ................................. 2011-074550
Mar. 30, 2011  (JP) ................................. 2011-074834

(51) Int. Cl.
*C08F 12/24*    (2006.01)
*C08F 12/30*    (2006.01)
(Continued)

(52) U.S. Cl.
CPC .......... *G03G 9/09775* (2013.01); *C07C 311/29* (2013.01); *C07C 311/51* (2013.01);
(Continued)

(58) Field of Classification Search
CPC .......... C08F 12/22; C08F 12/26; C08F 12/30; C08F 12/24; C08F 2220/585; C08F 220/54; C07C 311/51; C07C 311/52; C07C 311/48; C07C 311/49; C07C 311/29; C07C 311/28; G03G 9/08726; G03G 9/08728; G03G 9/08735; G03G 9/08795; G03G 9/08797; G03G 9/09775
See application file for complete search history.

(56) References Cited

U.S. PATENT DOCUMENTS 5,976,749 A    11/1999  Sukata et al.
6,541,491 B1 *  4/2003  Davies et al. ................. 514/340
(Continued)

FOREIGN PATENT DOCUMENTS

CN    101305023 A    11/2008
JP    3-105355 A     5/1991
(Continued)

OTHER PUBLICATIONS

European Search Report dated Sep. 26, 2014 in European Application No. 12765581.9.
(Continued)

*Primary Examiner* — Ling Choi
*Assistant Examiner* — David L Miller
(74) *Attorney, Agent, or Firm* — Fitzpatrick, Cella, Harper and Scinto

(57) ABSTRACT

To provide a polymeric compound having superior charge-providing properties, the polymeric compound contains at least one unit represented by the following general formula (5).

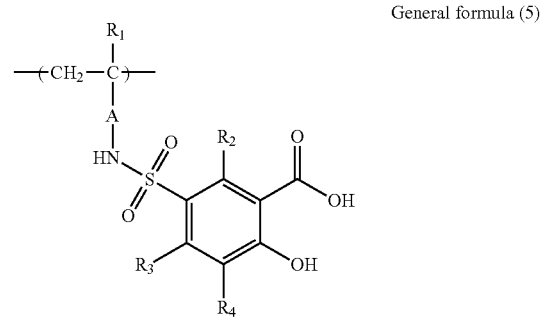

General formula (5)

In the general formula (5), $R_1$ represents a hydrogen atom or an alkyl group; $R_2$ to $R_4$ each represent a hydrogen atom, an alkyl group, an alkoxy group, a hydroxyl group or a halogen atom, or $R_3$ and $R_4$ may combine each other to form a ring; and A represents a divalent linking group.

11 Claims, 5 Drawing Sheets

(51) Int. Cl.

| | | |
|---|---|---|
| *C07C 311/51* | (2006.01) | |
| *G03G 9/097* | (2006.01) | |
| *C08F 12/22* | (2006.01) | |
| *C08F 12/26* | (2006.01) | |
| *C08F 212/08* | (2006.01) | |
| *C08F 212/12* | (2006.01) | |
| *C08F 212/14* | (2006.01) | |
| *C08F 212/32* | (2006.01) | |
| *C07C 311/29* | (2006.01) | |
| *C08F 220/58* | (2006.01) | |
| *C08F 220/54* | (2006.01) | |
| *C07C 311/52* | (2006.01) | |
| *C07C 311/48* | (2006.01) | |
| *C07C 311/49* | (2006.01) | |
| *C07C 311/28* | (2006.01) | |
| *G03G 9/087* | (2006.01) | |

(52) U.S. Cl.
CPC ............... *C08F 12/22* (2013.01); *C08F 12/24* (2013.01); *C08F 12/26* (2013.01); *C08F 12/30* (2013.01); *C08F 212/08* (2013.01); *C08F 212/12* (2013.01); *C08F 212/14* (2013.01); *C08F 212/32* (2013.01); *C08F 220/58* (2013.01); *G03G 9/08726* (2013.01); *G03G 9/08735* (2013.01); *G03G 9/08795* (2013.01); *G03G 9/08797* (2013.01); *C07C 311/28* (2013.01); *C07C 311/48* (2013.01); *C07C 311/49* (2013.01); *C07C 311/52* (2013.01); *C08F 220/54* (2013.01); *C08F 2220/585* (2013.01); *G03G 9/08728* (2013.01)

(56) References Cited

U.S. PATENT DOCUMENTS

| | | |
|---|---|---|
| 6,916,587 B2 | 7/2005 | Fushimi et al. |
| 7,300,991 B2 | 11/2007 | Nishimura et al. |
| 7,935,771 B2 | 5/2011 | Fukui et al. |
| 2003/0194610 A1 | 10/2003 | Nishimura et al. |
| 2014/0011129 A1 | 1/2014 | Murai et al. |

FOREIGN PATENT DOCUMENTS

| | | |
|---|---|---|
| JP | 4-16858 A | 1/1992 |
| JP | 2694572 B2 | 12/1997 |
| JP | 10-20560 A | 1/1998 |
| JP | 2003-5445 A | 1/2003 |
| JP | 2004-6273 A | 1/2004 |
| JP | 2005-157310 A | 6/2005 |
| JP | 2006-160854 | 6/2006 |
| JP | 4004080 B2 | 11/2007 |
| JP | 2009-186725 A | 8/2009 |
| JP | 2010-185907 A | 8/2010 |
| JP | 2010-250087 A | 11/2010 |

OTHER PUBLICATIONS

Peyser, "Glass Transition Temperatures of Polymers", Polymer Handbook, 3rd Edition, J. Brandup and E.H. Immergut (eds.), John Wiley & Sons, New York, 1989, pp. VI 209-VI 277.

Chinese Office Action dated Sep. 3, 2014 in Chinese Application No. 201280016609.7.

PCT International Search Report and Written Opinion of the International Searching Authority, International Application No. JP2012/058792, Mailing Date Jun. 5, 2012.

* cited by examiner

POLYMERIZABLE MONOMER, POLYMERIC COMPOUND, CHARGE CONTROL AGENT CONTAINING THE POLYMERIC COMPOUND, AND DEVELOPER BEARING MEMBER AND TONER WHICH CONTAIN THE CHARGE CONTROL AGENT

TECHNICAL FIELD

The present invention relates to a novel polymerizable monomer having a salicylic acid unit, and a polymeric compound produced by polymerizing the same. The present invention also relates to a charge control agent used in recording methods making use of electrophotography or the like, and a developer bearing member and a toner which contain the same.

BACKGROUND ART

In methods of forming images by electrophotography, electrostatic printing or the like, a developer charged electrostatically (hereinafter "toner") flies to the surface of a photosensitive drum by electrostatic force which accords with potential differences on the drum surface, and develops electrostatic latent images formed on the drum surface. Hence, it is necessary and indispensable to control charge characteristics of the toner. Then, as a method for providing the toner with proper charge characteristics, a method is known in which a surface layer of a developer bearing member (hereinafter also "developing roller") or the toner itself is incorporated with a charge control agent.

Conventionally, as negatively charging charge control agents, metal complexes of monoazo dyes, metal complexes of salicylic acid, alkylsalicylic acids or benzilic acid and so forth are used (PTL 1).

Recently, because of safety, concern about environments and a requirement for stabler charge characteristics, it is proposed to use as the charge control agent a resin having charge control function. In PTL 2, it is proposed that a resin having a sulfonic acid group is added to a surface layer of the developing roller to thereby make the toner improved in its uniformity of triboelectric charging and its running stability.

Meanwhile, in recent years, images to be reproduced are desired to be of much higher image quality, and faulty images have come into question, such that "fog" occurs where the toner comes into development at blank or white areas of images and that any streaky density non-uniformity occurs on images. What is a large factor of such a phenomenon is the occurrence of a toner having come charged to a polarity reverse to the desired charge polarity.

For the purpose of making a toner charged to a reverse polarity less occur or keeping the toner from being so charged, PTL 3 discloses therein an example in which a salicylic acid metal complex is used as a charge control agent, and PTL 4 discloses therein an example in which a polymeric compound composed of a monomer unit having a sulfonic acid group is used as a charge control agent. PTL 5 also discloses therein an example in which a polymeric compound to the polymeric backbone chain of which a salicylic acid unit is directly bonded is used in the toner.

CITATION LIST

Patent Literature

PTL 1: Japanese Patent No. 4004080
PTL 2: Japanese Patent Application Laid-open No. 2005-157310
PTL 3: Japanese Patent Application Laid-open No. H10-020560
PTL 4: Japanese Patent Application Laid-open No. 2003-005445
PTL 5: Japanese Patent No. 2694572

SUMMARY OF INVENTION

Technical Problem

In the above charge control agents used conventionally, it can not be said for them to have, for the toner, any charge-providing properties that can satisfy the desires in recent years for higher speed and higher image quality, and it is sought to make further improvement or make development of a novel polymeric compound.

Accordingly, an object of the present invention is to provide a novel polymerizable monomer that can obtain a polymeric compound having better charge-providing properties than any conventional charge control agents, and a polymeric compound obtained therefrom.

Another object of the present invention is to provide a developer bearing member having a superior charge-providing performance to the toner inasmuch as a charge control agent containing such a polymeric compound is used in the developer bearing member.

A further object of the present invention is to provide a toner which contains such a polymeric compound, has a high charging rise speed, shows a high saturated charge quantity, and at the same time can be made less in proportion about particles having come charged to a polarity reverse to the desired charge polarity.

Solution to Problem

The present invention is concerned with a polymerizable monomer represented by the following general formula (1).

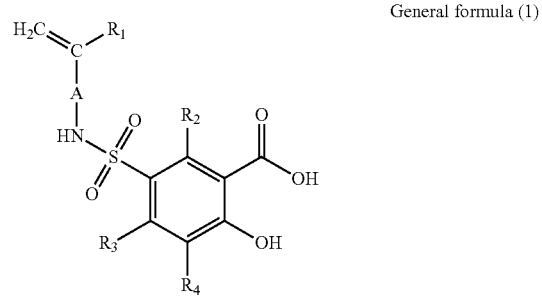

General formula (1)

The present invention is also concerned with a polymeric compound having at least one unit represented by the following general formula (5).

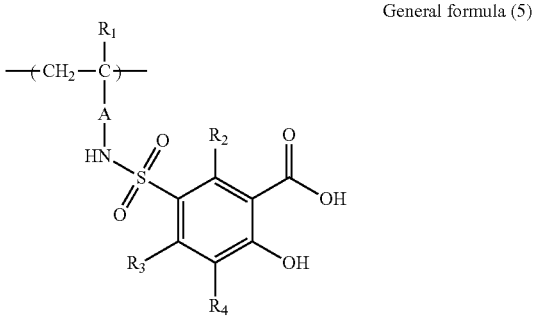

General formula (5)

In the general formulas (1) and (5), $R_1$ represents a hydrogen atom or an alkyl group; $R_2$ to $R_4$ each represent a hydrogen atom, an alkyl group, an alkoxy group, a hydroxyl group or a halogen atom, or $R_3$ and $R_4$ may combine each other to form a ring; and A represents a divalent linking group.

The present invention is further concerned with a charge control agent containing the polymeric compound having the above unit, and a developer bearing member and a toner which contain the charge control agent.

Advantageous Effects of Invention

The present invention enables a polymeric compound to be provided which has good charge-providing properties.

The present invention also enables a charge control agent to be provided which can properly control the charge characteristics of a developer or the charge-providing performance of a developer bearing member.

The present invention further enables a developer bearing member to be provided which has a superior charge-providing performance to the toner inasmuch as the charge control agent is used in the developer bearing member.

Meanwhile, a toner is provided which has a high charging rise speed, shows a high saturated charge quantity, and at the same time can be made less in proportion about particles having come charged to a polarity reverse to the desired charge polarity, inasmuch as the above polymeric compound is incorporated in the toner.

Further features of the present invention will become apparent from the following description of exemplary embodiments with reference to the attached drawings.

DESCRIPTION OF EMBODIMENTS

Figure 1:
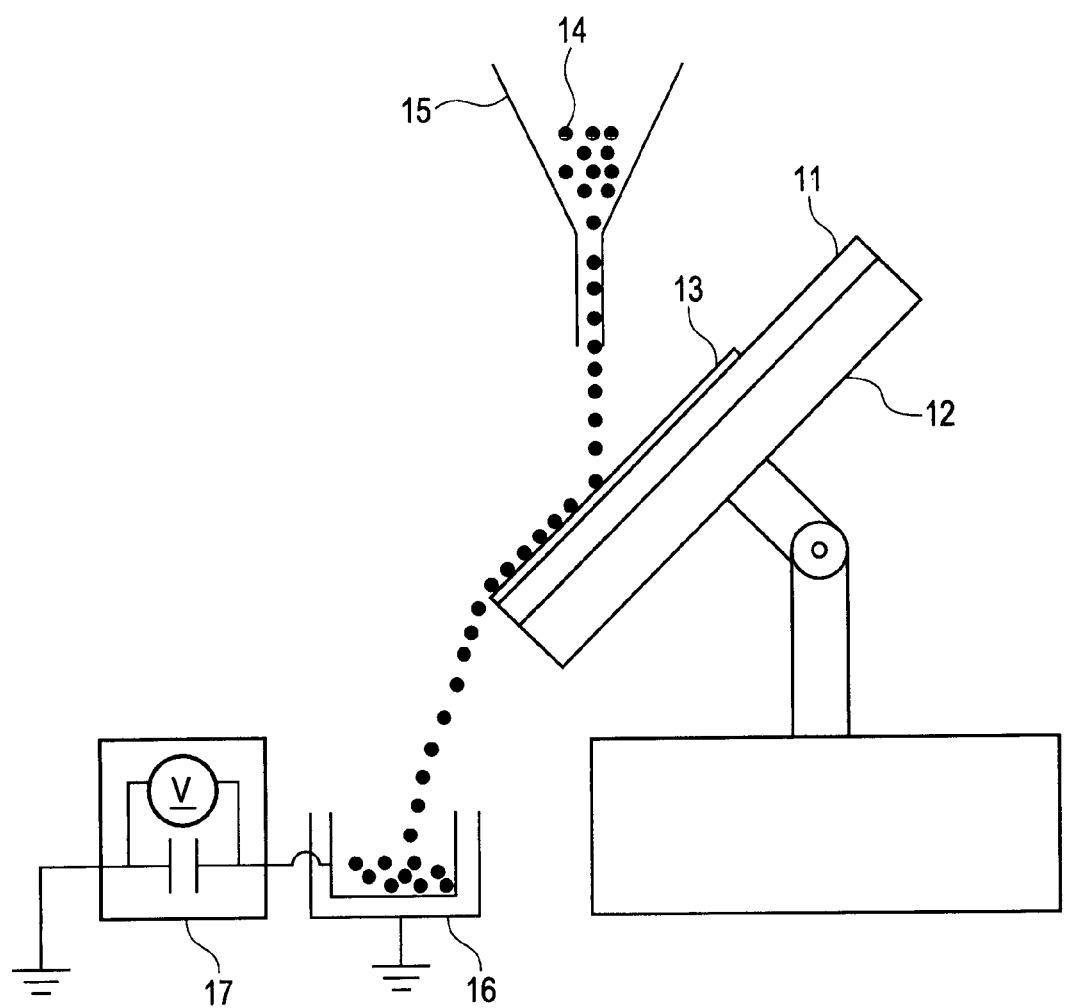
FIG. 1 is a view showing a cascade type charge quantity measuring instrument used to evaluate the charge characteristics of the polymeric compound of the present invention.

The present invention is described below in detail by giving preferred embodiments.

The present inventors have made extensive studies in order to resolve the above problems the prior art has had. As the result, they have discovered that a polymeric compound produced by polymerizing a polymerizable monomer represented by the following general formula (1) and having at least one unit represented by the following general formula (5) shows good charge characteristics. The present polymerizable monomer and polymeric compound are described below in detail.

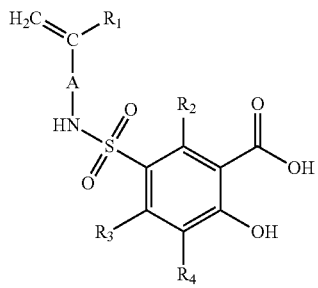

General formula (1)

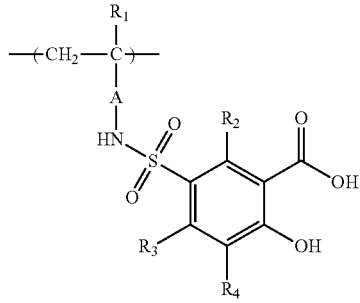

General formula (5)

In the general formulas (1) and (5), $R_1$ represents a hydrogen atom or an alkyl group; $R_2$ to $R_4$ each represent a hydrogen atom, an alkyl group, an alkoxy group, a hydroxyl group or a halogen atom, or $R_3$ and $R_4$ may combine each other to form a ring; and A represents a divalent linking group.

The alkyl group represented by $R_1$ may include, e.g., a methyl group, an ethyl group, a n-propyl group, an isopropyl group and a n-butyl group. $R_1$ may be selected as desired from the substituents enumerated above and a hydrogen atom, where a case in which it is a hydrogen atom or a methyl group is preferred from the viewpoint of the polymerizability of the polymerizable monomer.

The alkyl group represented by $R_2$ to $R_4$ each may include, e.g., a methyl group, an ethyl group, a n-propyl group, an isopropyl group, a n-butyl group, an isobutyl group, a sec-butyl group and a tert-butyl group.

The alkoxy group represented by $R_2$ to $R_4$ each may include, e.g., a methoxy group, an ethoxy group, a n-propoxy group and an isopropoxy group.

The hydrogen atom represented by $R_2$ to $R_4$ each may include, e.g., a fluorine atom, a chlorine atom, a bromine atom and an iodine atom.

Where $R_2$ to $R_4$ are each an alkyl group or an alkoxy group, it may further be substituted, and there are no particular limitations thereon as long as the polymerizable monomer is not inhibited from being polymerizable or the polymeric compound is not extremely made low in its charge characteristics. In this case, a substituent which may serve on such substitution may include alkoxy groups such as a methoxy group and an ethoxy group, amino groups such as an N-methylamino group and an N,N-dimethylamino group, an acyl groups such as an acetyl group, and halogen atoms such as a fluorine atom and a chlorine atom.

$R_3$ and $R_4$ may combine each other to form a ring. A group that forms the ring may be an alkylene group having 3 to 8 carbon atoms, or a hetero ring in an alkylene chain of which an oxygen atom or a sulfur atom is present.

As the linking group A, there are no particular limitations thereon as long as it is a divalent linking group, and a case in which it is such a linking group that the polymerizable monomer is represented by any of the following general formulas (2) to (4) is preferred from the viewpoint of the readiness in obtaining raw materials or producing it.

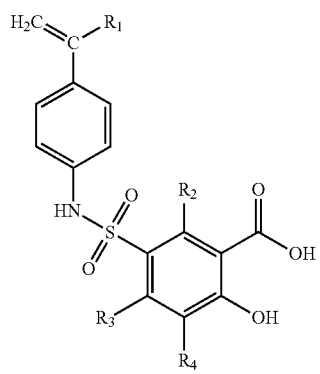

General formula (2)

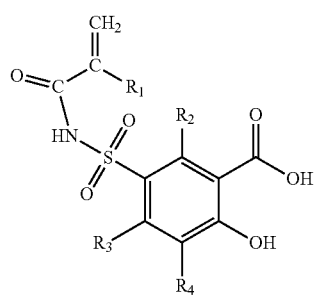

General formula (3)

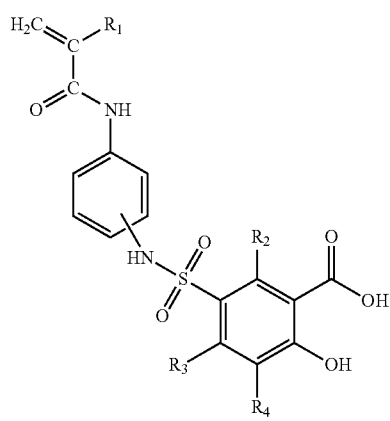

General formula (4)

The polymeric compound of the present invention may be a copolymer containing at least one of each of the unit represented by the general formula (5) and a unit represented by the following general formula (6).

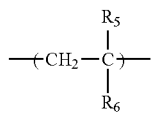

General formula (6)

In the general formula (6), $R_5$ represents a hydrogen atom or an alkyl group; and $R_6$ represents a phenyl group, a carboxyl group, a carboxylate group or a carboxylic acid amide group.

The alkyl group represented by $R_5$ may include, e.g., a methyl group, an ethyl group, a n-propyl group, an isopropyl group and a n-butyl group. $R_5$ may be selected as desired from the substituents enumerated above and a hydrogen atom, where a hydrogen atom or a methyl group is preferred from the viewpoint of the polymerizability of the polymerizable monomer.

The carboxylate group represented by $R_6$ may include ester groups such as a methyl ester group, an ethyl ester group, a n-propyl ester group, an isopropyl ester group, a n-butyl ester group, an isobutyl ester group, a sec-butyl ester group, a tert-butyl ester group, a dodecyl ester group, a 2-ethylhexyl ester group, a stearyl ester group, a phenyl ester group and a 2-hydroxyethyl ester group.

The carboxylic acid amide group represented by $R_6$ may include amide groups such as an N-methyl amide group, an N,N'-dimethyl amide group, an N,N'-diethyl amide group, an N-isopropyl amide group, an N-tert-butyl amide group and an N-phenyl amide group.

Where $R_6$ is the above substituent, it may further be substituted, and there are no particular limitations thereon as long as the polymerizable monomer is not inhibited from being polymerizable or the polymeric compound is not extremely made low in its charge characteristics. A substituent in this case may include alkoxy groups such as a methoxy group and an ethoxy group, amino groups such as an N-methylamino group and an N,N-dimethylamino group, acyl groups such as an acetyl group, and halogen atoms such as a fluorine atom and a chlorine atom.

In view of the dispersibility in a binder resin of a surface layer of the developer bearing member and in a binder resin of the toner, $R_6$ may be a phenyl group or a carboxylate group. Such a case is preferable. That is, a case is preferable in which the unit represented by the general formula (6) is a styrene derivative unit or an acrylate derivative unit.

The monomer unit represented by the general formula (5) may preferably be in a content of from 0.01 mol % to 30 mol %, and much preferably from 0.01 mol % to 10 mol %, based on the whole monomer units constituting the copolymer. As long as it is within the above range, good charge characteristics can be achieved and, in addition thereto, good dispersibility and compatibility can be achieved also for the binder resin of the developer bearing member surface layer and for the binder resin of the toner.

The polymeric compound of the present invention may preferably have molecular weight in the range of from 3,000 to 100,000, and much preferably in the range of from 5,000 to 50,000, as weight-average molecular weight. As long as it is within the above range, it can well be dispersed in the developer bearing member surface layer or in toner particle surface layers, and is well kept from coming off the developer bearing member surface layer or toner particle surfaces.

How to produce the present polymerizable monomer is described below in detail.

The polymerizable monomer according to the present invention, represented by the general formula (1), may be synthesized according to a known method. An example of a synthesis scheme is shown below.

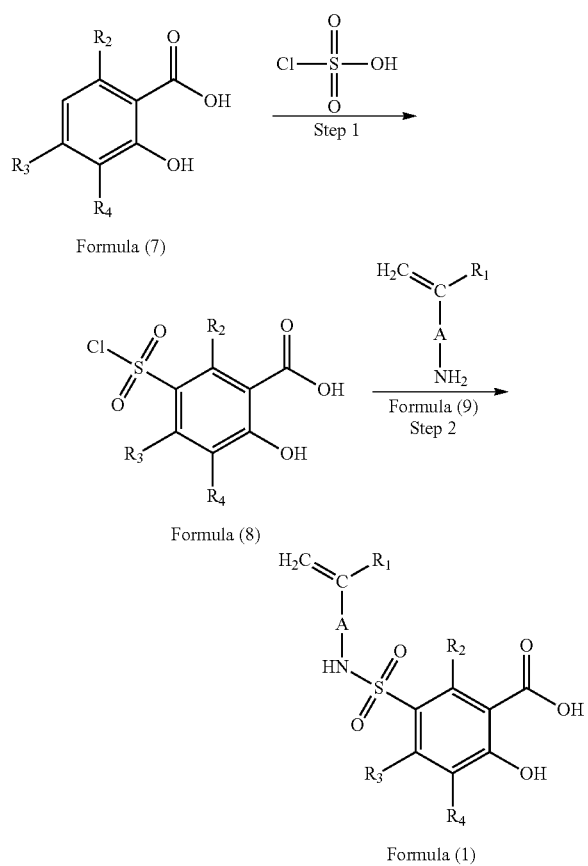

In the general formulas (7) to (9), $R_1$ to $R_4$ each represent the same as those in the general formula (1).

In the synthesis scheme shown above, the polymerizable monomer represented by the general formula (1) may be synthesized through a step 1 in which a salicylic acid derivative represented by the formula (7) is chlorosulfonated to obtain a formula-(8) intermediate and a step 2 in which the formula-(8) intermediate is made into an amide with an amine derivative having a vinyl group, represented by the formula (9).

The step 1 is described first. As the step 1, a known method may be utilized (see, e.g., "New Experimental Chemistry Course", Maruzen Co., Ltd., Third Edition, Vol. 14-3, pp.1787-1788).

The formula-(7) salicylic acid derivative is commercially available in many kinds and is obtainable with ease. It may also be synthesized by a known method.

This step 1 may preferably be carried out without any solvent, or may also be carried out in a solvent when it is difficult to control reaction temperature or when otherwise any by-product is formed. There are no particular limitations on the solvent as long as it does not inhibit the reaction, which may preferably be a halogenated hydrocarbon type solvent as exemplified by dichloromethane, chloroform or carbon tetrachloride. The solvent may preferably be used in an amount determined as desired, which may preferably be in the range of from 1.0-fold by mass to 20-fold by mass based on the mass of the formula-(7) salicylic acid derivative, from the viewpoint of production efficiency.

This reaction is usually carried out in a temperature range of from −20° C. to 180° C., and is usually completed within 24 hours.

The step 2 is described next. As the step 2, a known method may be utilized (see, e.g., "New Experimental Chemistry Course", Maruzen Co., Ltd., Third Edition, Vol. 14-3, pp.1803-1804).

The formula-(9) amine derivative having a vinyl group is commercially available in many kinds and is obtainable with ease. It may also be synthesized by a known method.

This step 2 may preferably be carried out without any solvent, but may preferably be carried out in a solvent in order to prevent the reaction from proceeding abruptly. There are no particular limitations on the solvent as long as it does not inhibit the reaction, which may include, e.g., water; esters such as methyl acetate, ethyl acetate and propyl acetate; ketones such as acetone and methyl ethyl ketone; ethers such as diethyl ether, tetrahydrofuran and dioxane; hydrocarbons such as benzene, toluene, xylene, hexane and heptane; and amides such as N,N-dimethylformamide and N,N-dimethylimidasolidinone. Any of these solvents may also be used in the form of a mixture of two or more types, and their mixing ratio may be determined as desired, when used mixedly. The solvent may be used in an amount determined as desired, depending on the solubility of substrate, which may preferably be in the range of from 1.0-fold by mass to 20-fold by mass based on the mass of the formula-(8) intermediate, from the viewpoint of production efficiency.

This step 2 may be carried out in a temperature range of from −20° C. to 200° C., and may preferably be carried out in a temperature range of from −20° C. to 60° C. in order to prevent the formula-(1) polymerizable monomer and an amine derivative-(9) from being thermally polymerized. Also, the reaction is usually completed within 24 hours.

In this step 2, a polymerization inhibitor may be used in order to prevent the formula-(1) polymerizable monomer and an amine derivative-(9) from being polymerized during the reaction. The polymerization inhibitor may include quinones such as p-benzoquinone, naphthoquinone and 2,5-diphenyl-p-benzoquinone; and polyhydric phenols such as hydroquinone, p-tert-butylcatechol and 2,5-di-tert-butylhydroquinone. The polymerization inhibitor may be added in an amount determined as desired, which may preferably be in the range usually of from 10 ppm to 5,000 ppm based on the formula-(1) polymerizable monomer or an amine derivative-(9).

In this step 2, hydrogen chloride formed during the reaction may be removed with a base, whereby the reaction can be accelerated. The base may include alkali hydroxides such as sodium hydroxide and potassium hydroxide, and organic bases such as pyridine, triethylamine and N,N-diisopropylethylamine. The formula-(9) amine derivative may also be used in excess as the base. Any of the bases may be used in the form of a mixture of two or more types, and their mixing ratio may be determined as desired, when used mixedly. The base may be used in an equimolar amount or more, based on the formula-(8) intermediate, and may be used also as a reaction solvent in place of the above solvent.

The compounds represented by the formulas (1), (7) and (8), used or obtained in the respective steps, may be isolated and purified by a conventional process of isolation and purification of organic compounds. Such an isolation and purification process may include, e.g., recrystallization or reprecipitation, and column chromatography making use of an adsorbent such as silica gel. The purification may be carried out by any of these methods alone or in combination of two or more processes to obtain the intended compounds in a high purity.

The compounds represented by the formulas (1), (7) and (8), used or obtained in the respective steps, may be identified by instrumental analysis of various types. As an analytical instrument usable therefor, a $^1H$ and $^{13}C$ nuclear magnetic resonance (NMR) instrument, a high-speed liquid chromatograph (HPLC), a mass spectrograph (MS) or the like may be used.

How to produce the polymeric compound of the present invention is described below in detail.

As a polymerization process for the polymeric compound of the present invention, it may include radical polymerization and ionic polymerization. Living polymerization may also be used which is intended for molecular weight distribution control or structural control. It is industrially preferable to use radical polymerization.

The radical polymerization used in the present invention may be carried out by using a radical polymerization initiator, by irradiation with radiations, laser light or the like, by using a photopolymerization initiator and light irradiation in combination, by heating and so forth.

As the radical polymerization initiator used in the present invention, any agent may be used as long as it can produce radicals and initiate the polymerization reaction, and may be selected from compounds capable of producing radicals by the action of heat, light, radiation, oxidation-reduction reaction or the like. For example, it may include azo compounds, organic peroxides, inorganic peroxides, organometallic compounds and photopolymerization initiators. Stated more specifically, it may include azo compounds such as 2,2'-azobisisobutyronitrile (AIBN) and 2,2'-azobis(2,4-dimethylvaleronitrile); organic peroxides such as benzoyl peroxide (BPO), tert-butyl peroxypivarate and tert-butyl peroxyisopropyl carbonate; inorganic peroxides such as potassium persulfate and ammonium persulfate; and redox initiators such as a hydrogen peroxide-iron(II) salt type, BPO-dimethylaniline type and a cerium(IV) salt-alcohol type. The photopolymerization initiator may include an acetophenone type, a benzoin ether type and a ketal type. Any of these radical polymerization initiators used in the present invention may be used in combination of two or more types.

As to polymerization temperature for the polymeric compound of the present invention, its preferable temperature range may differ depending on the type of the polymerization initiator to be used, and there are no particular limitations thereon, and it is common to carry out the polymerization at a temperature of from −30° C. to 180° C. Much preferable temperature range is from 40° C. to 150° C.

As to the amount of the polymerization initiator to be used here, it is from 0.1 part by mass to 20 parts by mass based on 100 parts by mass of the monomer, and may preferably be so controlled that the polymeric compound having the intended molecular weight distribution can be obtained.

As the polymerization process therefor, any of processes such as solution polymerization, suspension polymerization, emulsion polymerization, dispersion polymerization, precipitation polymerization and bulk polymerization may be used, and there are no particular limitations thereon.

The polymeric compound obtained may optionally be subjected to purification treatment. There are no particular limitations on a purification process therefor, and a process such as reprecipitation or column chromatography may be used.

The structure of the polymeric compound produced may be identified by instrumental analysis of various types. As an analytical instrument usable therefor, a $^1H$ and $^{13}C$ nuclear magnetic resonance (NMR) instrument, size exclusion chromatography (SEC) or the like may be used.

The polymeric compound of the present invention may be incorporated in the surface layer of a developer bearing member, and this enables a developer to be provided with electric charges in a proper quantity to make this polymeric compound act as a charge control agent for the developer. This polymeric compound may also be incorporated in a toner as a charge control agent, and this enables the toner to be controlled to have a proper charge quantity.

In the case when the present polymeric compound is used as a charge control agent, the type of the unit represented by the general formula (6) may appropriately be selected, and this enables control of the compatibility with and dispersibility in the binder resin of the developer bearing member surface layer and the binder resin of the toner.

Such a developer bearing member containing in its surface layer at least one type of the charge control agent of the present invention can quickly provide the developer with electric charges in a proper quantity, and images are obtained which have a high image density and less fog.

The charge control agent of the present invention brings out its effect by incorporating it in the outermost surface layer of a developing roller or developing sleeve on which the developer is to be held, without regard to the types of developing systems such as one-component development, two-component development, development making use of a magnetic developer or a non-magnetic developer, and development making use of a positively chargeable developer or negatively chargeable developer. In particular, the present charge control agent acts most effectively when it is applied to a non-magnetic one-component developing system making use of a positively chargeable developer. The developer bearing member of the present invention is described below taking the case of the above developing roller.

In the above developing system, the developing roller is so disposed on a photosensitive drum as to be pressed against it and, while being rotated, develops and renders visible the electrostatic latent images formed on the developing roller, with the positively chargeable developer held on its surface. Hence, the developing roller may most preferably be so constituted as to have an elastic layer on a cylindrical shaft and also have a surface layer thereon.

The shaft of the developing roller may suffice as long as it has strength high enough to endure molding and actual service, and may preferably be made up of a rigid and electrically conductive material of 4 mm to 10 mm in outer diameter. A material for the shaft may include, e.g., metals such as iron, aluminum, titanium, cupper and nickel; alloys containing any of these metals, such as stainless steel, duralmin, brass and bronze; and composite materials obtained by hardening carbon black or carbon fiber with a plastic.

The elastic layer of the developing roller may be formed of a known rubber material. A rubber material usable therefor may include natural rubber, silicone rubber, urethane rubber, ethylene propylene rubber, butadiene rubber, chloroprene rubber, isoprene rubber and nitrile rubber.

The elastic layer may preferably be electrically conductive, and carbon black, graphite, a metal powder, a conductive metal oxide, a conductive rubber or the like may be added thereto for the purpose of providing it with electrical conductivity.

The elastic layer may preferably have a layer thickness of from 2 mm to 10 mm. If it has a layer thickness of more than 10 mm, it may have too high resistance value, and if it has a layer thickness of less than 2 mm, it may have no sufficiently low hardness to come in low close contact with the photosensitive drum.

The surface layer of the developing roller is constituted of the charge control agent of the present invention, a conductivity-providing agent, surface-roughening particles, and a binder resin.

The charge control agent may be added to the surface layer of the developing roller of the present invention in an amount of usually from 0.01 part by mass to 50 parts by mass, and preferably from 0.05 part by mass to 30 parts by mass, based on 100 parts by mass of the binder resin. As long as its amount is within the above range, the charge control agent is well achievable of both securing its charge-providing ability and keeping itself from releasing from the surface layer.

As the conductivity-providing agent usable in the surface layer, carbon black, graphite, a metal powder, a conductive metal oxide, a conductive rubber or the like may be used, as having been given as the conductivity-providing agent of the above elastic layer.

The surface-roughening particles may include, e.g., rubber particles of silicone rubber, urethane rubber, ethylene propylene rubber, butadiene rubber, chloroprene rubber, isoprene rubber, nitrile rubber or the like; elastomer particles of thermoplastic elastomers of polystyrene, polyolefin, polyvinyl chloride, polyurethane, polyester and polyamide types; resin particles of fluorine resin, silicone resin, phenol resin, naphthalene resin, furan resin, xylene resin, divinylbenzene polymer, styrene-divinylbenzene copolymer, polyacrylonitrile resin or the like; and low-density and well electrically conductive spherical carbon particles obtained by carbonizing and/or graphitizing such resin type spherical particles or mesocarbon microbeads by firing them.

As to the surface-roughening particles, its particle size distribution and amount may preferably be so controlled that the surface layer has ten-point average surface roughness (hereinafter "Rz") in the range of from 1 μm to 30 μm.

As the binder resin, there are no particular limitations thereon as long as it can follow up any flexible deformation of the elastic layer, and it may preferably be a resin which does not contaminate the photosensitive drum upon contact of the elastic layer with the photosensitive drum. For example, it may include urethane resins and fluororubber resins, having a low cross-link density and being flexible.

The surface layer of the developing roller may have a layer thickness of from 5 μm to 500 μm, and preferably from 10 μm to 200 μm. As long as its layer thickness is within the above range, the developing roller may easily secure an appropriate hardness as the roller, and may also easily secure a sufficient durability.

The developing roller of the present invention is produced by forming the elastic layer on a mandrel serving as the shaft, and thereafter coating it with a surface layer composition, followed by drying or curing.

Such a surface layer composition is one prepared by dissolving or dispersing the above charge control agent, conductivity-providing agent, surface-roughening particles and binder resin in a solvent. As the solvent usable therefor, there are no particular limitations thereon as long as it is a solvent capable of sufficiently dissolving or dispersing the materials for the surface layer composition, and any of organic solvents such as toluene, methyl ethyl ketone, ethyl acetate and isopropyl alcohol may be used.

In preparing the surface layer composition, a known dispersion machine such as a ball mill, a paint shaker, a dissolver, an attritor, a sand mill or a high-speed mill may be used, and there are no particular limitations thereon as long as it can sufficiently dissolve or disperse the materials.

The surface layer composition may be coated by a coating method such as spray coating or dipping, which may appropriately be selected in accordance with the viscosity of the surface layer composition and the layer thickness of the intended surface layer.

The toner of the present invention is described next.

The toner of the present invention is a toner containing the above polymeric compound as a charge control agent. The use of this polymeric compound can provide a toner having a high charging rise speed, showing a high saturated charge quantity and also making reverse-polarity toner less form. Toner base particles constituting the toner of the present invention further contain toner-constituting components such as a binder resin, a colorant and a wax.

In the toner of the present invention, an optimal toner triboelectric charge quantity that accords the developing system can be controlled by the amount of the above polymeric compound to be added. The polymeric compound in the toner of the present invention may be added in an amount of usually from 0.01 part by mass to 50 parts by mass, preferably from 0.03 part by mass to 30 parts by mass, and much preferably from 0.05 part by mass to 10 parts by mass, based on 100 parts by mass of the total mass of the binder resin.

In the method of obtaining the toner particles directly by polymerization, the polymerizable monomer of the present invention may be added to a toner production step together with a polymerizable monomer serving as the binder resin of the toner. In such a case, the former polymerizable monomer of the present invention may be added in an amount usually from 0.001% by mass to 5% by mass, preferably from 0.003% by mass to 3% by mass, and much preferably from 0.005% by mass to 1% by mass, based on the total mass of the binder resin.

The toner of the present invention exhibits sufficient charge characteristics by incorporating the above polymeric compound alone, but, in accordance with the developing system in which the toner of the present invention is used, may use it in combination with any existing charge control agent for the purpose of controlling the charge characteristics. Such a charge control agent usable in combination may include, e.g., the following.

As a negatively charging charge control agent, it may include polymeric compounds having a sulfonic acid group, a sulfonic salt group or a sulfonic ester group; salicylic acid derivatives and metal complexes thereof; monoazo metal compounds; acetylacetone metal compounds; aromatic hydroxycarboxylic acids, aromatic mono- and polycarboxylic acids, and metal salts, anhydrides or esters thereof; phenol derivatives such as bisphenol; and also urea derivatives, boron compounds and carixarene.

As a positively charging charge control agent, it may include Nigrosine and Nigrosine-modified products, modified with a fatty acid metal salt or the like; guanidine compounds; imidazole compounds; quaternary ammonium salts such as tributylbenzylammonium 1-hydroxy-4-naphthosulfonate and tetrabutylammonium tetrafluoroborate, and analogues of these, including onium salts such as phosphonium salts, and lake pigments of these; triphenylmethane dyes and lake pigments of these (lake-forming agents may include tungstophosphoric acid, molybdophosphoric acid, tungstomolybdophosphoric acid, tannic acid, lauric acid, gallic acid, ferricyanides and ferrocyanides); metal salts of higher fatty acids; diorganotin oxides such as dibutyltin oxide, dioctyltin oxide and dicyclohexyltin oxide; and diorganotin borates such as dibutyltin borate, dioctyltin borate and dicyclohexyltin borate.

The components constituting the toner of the present invention are described below in detail.

As the binder resin usable in the toner of the present invention, a known resin may be used, where usable are a vinyl resin such as styrene-acrylic resin, a polyester resin, and a hybrid resin formed of combination of these.

In the method of obtaining the toner particles directly by polymerization, monomer(s) for forming them is/are used. Such monomer(s) may specifically include styrene; styrene monomers such as o-, m- or p-methylstyrene, and o-, m- or p-ethylstyrene; acrylate monomers such as methyl acrylate, ethyl acrylate, propyl acrylate, butyl acrylate, octyl acrylate, dodecyl acrylate, stearyl acrylate, behenyl acrylate, 2-ethylhexyl acrylate, dimethylaminoethyl acrylate, diethylaminoethyl acrylate, acrylonitrile and acrylic acid amide; methacrylate monomers such as methyl methacrylate, ethyl methacrylate, propyl methacrylate, butyl methacrylate, octyl methacrylate, dodecyl methacrylate, stearyl methacrylate, behenyl methacrylate, 2-ethylhexyl methacrylate, dimethylaminoethyl methacrylate, diethylaminoethyl methacrylate, methacrylonitrile and methacrylic acid amide; and olefinic monomers such as butadiene, isoprene and cyclohexene.

Any of these may be used alone, or may commonly be used in the form of an appropriate mixture of monomers which are so mixed that the theoretical glass transition temperature (Tg) as described in "POLYMER HANDBOOK" Edited by J. Brandrup and E. H. Immergut, (U.S.A.), Third Edition, John Wiley & Sons, Inc., 1989, pp.209-277, may stand in the range of from 40° C. to 75° C. If the theoretical glass transition temperature is less than 40° C., a problem tends to arise in view of the storage stability or running stability of the toner. If on the other hand it is more than 75° C., images may be of low transparency when full-color images of toners are formed.

Further, in the present invention, in order to enhance the mechanical strength of the toner particles and also control the molecular weight of the binder resin, a cross-linking agent may also be used when the binder resin is synthesized.

As the cross-linking agent used in the toner of the present invention, it may include, as a bifunctional cross-linking agent, divinylbenzene, 2,2-bis(4-acryloxyethoxyphenyl)propane, 2,2-bis(4-methacryloxyphenyl)propane, diallyl phthalate, ethylene glycol diacrylate, 1,3-butylene glycol diacrylate, 1,4-butanediol diacrylate, 1,5-pentanediol diacrylate, 1,6-hexanediol diacrylate, neopentyl glycol diacrylate, diethylene glycol diacrylate, triethylene glycol diacrylate, tetraethylene glycol diacrylate, polyethylene glycol #200 diacrylate, polyethylene glycol #400 diacrylate, polyethylene glycol #600 diacrylate, dipropylene glycol diacrylate, polypropylene glycol diacrylate, polyester type diacrylates, and the above diacrylates each acrylate moiety of which has been replaced with methacrylate.

As a polyfunctional cross-linking agent, it may include pentaerythritol triacrylate, trimethylolethane triacrylate, trimethylolpropane triacrylate, tetramethylolmethane tetraacrylate, oligoester acrylate, and methacrylates of these, and also triallyl cyanurate, triallyl isocyanurate and triallyl trimellitate.

Any of these cross-linking agents may preferably be used in an amount of from 0.05 part by mass to 10 parts by mass, and much preferably from 0.1 part by mass to 5 parts by mass, based on 100 parts by mass of the above monomer, in view of the fixing performance and anti-offset properties of the toner.

The toner of the present invention may be either of a magnetic toner and a non-magnetic toner. Where it is used as the magnetic toner, a magnetic material which may include the following may preferably be used. That is, it may include iron oxides such as magnetite, maghemite and ferrite, or iron oxides including other metal oxides; metals such as Fe, Co and Ni, or alloys of any of these metals with any of metals such as Al, Co, Cu, Pb, Mg, Ni, Sn, Zn, Sb, Be, Bi, Cd, Ca, Mn, Se, Ti, W and V, and mixtures of any of these.

The magnetic material may specifically include, e.g., triiron tetraoxide ($Fe_3O_4$), γ-iron sesquioxide (γ-$Fe_2O_3$), zinc iron oxide ($ZnFe_2O_4$), yttrium iron oxide ($Y_3Fe_5O_{12}$), cadmium iron oxide ($CdFe_2O_4$), gadolinium iron oxide ($Gd_3Fe_5O_{12}$), copper iron oxide ($CuFe_2O_4$), lead iron oxide ($PbFe_{12}O_{19}$), nickel iron oxide ($NiFe_2O_4$), neodymium iron oxide ($NdFe_2O_3$), barium iron oxide ($BaFe_{12}O_{19}$), magnesium iron oxide ($MgFe_2O_4$), manganese iron oxide ($MnFe_2O_4$), lanthanum iron oxide ($LaFeO_3$), iron powder (Fe), cobalt powder (Co) and nickel powder (Ni). Any of the above magnetic materials may be used alone or in combination of two or more types. A magnetic material particularly preferable for what is aimed in the present invention is fine powder of triiron tetraoxide or γ-iron sesquioxide.

These magnetic materials may be those having an average particle diameter of from 0.1 μm to 2 μm (preferably from 0.1 μm to 0.3 μm), and a coercive force of from 1.6 kA/m to 12 kA/m, a saturation magnetization of from 5 $Am^2/kg$ to 200 $Am^2/kg$ (preferably from 50 $Am^2/kg$ to 100 $Am^2/kg$) and a residual magnetization of from 2 $Am^2/kg$ to 20 $Am^2/kg$, as magnetic properties under application of a magnetic field of 795.8 kA/m, which are preferable in view of the developing performance of the toner.

Any of these magnetic materials may be added in an amount of from 10 parts by mass to 200 parts by weight, and preferably from 20 parts by mass to 150 parts by weight, based on 100 parts by weight of the binder resin.

Where on the other hand the toner is used as the non-magnetic toner, any known colorant including conventionally known various dyes or pigments may be used as the colorant.

For example, as a colorant for magenta, it may include C.I. Pigment Red 1, 2, 3, 4, 5, 6, 7, 8, 9, 10, 11, 12, 13, 14, 15, 16, 17, 18, 19, 21, 22, 23, 30, 31, 32, 37, 38, 39, 40, 41, 48, 49, 50, 51, 52, 53, 54, 55, 57, 58, 60, 63, 64, 68, 81, 83, 87, 88, 89, 90, 112, 114, 122, 123, 163, 202, 206, 207, 209; C.I. Pigment Violet 19; and C.I. Vat Red 1, 2, 10, 13, 15, 23, 29, 35.

As a colorant for cyan, it may include C.I. Pigment Blue 2, 3, 15:1, 15:3, 16, 17, 25, 26; C.I. Vat Blue 6; C.I. Acid Blue 45; and copper phthalocyanine pigments the phthalocyanine skeleton of which has been substituted with 1 to 5 phthalimide methyl group(s).

As a colorant for yellow, it may include C.I. Pigment Yellow 1, 2, 3, 4, 5, 6, 7, 10, 11, 12, 13, 14, 15, 16, 17, 23, 65, 73, 74, 83, 93, 155, 180; C.I. Solvent Yellow 9, 17, 24, 31, 35, 58, 93, 100, 102, 103, 105, 112, 162, 163; and C.I., Vat Yellow 1, 3, 20.

As a black colorant, carbon black and a colorant toned in black by the use of yellow, magenta and cyan colorants shown above may be used.

Any of these colorants may suitably be used in an amount, which may differ depending on the types of the colorants, of from 0.1 part by mass to 60 parts by mass, and preferably from 0.5 part by mass to 50 parts by mass, in total mass based on 100 parts by mass of the binder resin.

As the wax component usable in the present invention, it may specifically include petroleum waxes such as paraffin wax, microcrystalline wax and petrolatum, and derivatives thereof; montan wax and derivatives thereof; hydrocarbon waxes obtained by Fischer-Tropsch synthesis, and derivatives thereof; polyolefin waxes as typified by polyethylene wax, and derivatives thereof; and naturally occurring waxes such as carnauba wax and candelilla wax, and derivatives thereof. The derivatives of these include oxides, block copolymers with vinyl monomers, and graft modified products. It may further include alcohols such as higher aliphatic alcohols, fatty acids such as stearic acid and palmitic acid, acid amides or fatty esters of these compounds, hardened caster oil and derivatives thereof, vegetable waxes, and animal waxes. Any of these may be used alone or in combination.

The wax component may preferably be added in such an amount that its content based on 100 parts by mass of the binder resin is from 2.5 parts by mass to 15.0 parts by mass, and much preferably from 3.0 parts by mass to 10.0 parts by mass, in total mass. If the wax component is added in an amount of less than 2.5 parts by mass, oilless fixing may be performed with difficulty, and if it is in an amount of more than 15.0 parts by mass, the wax component in the toner is in so large an amount that any excess wax component may come much present on the toner particles, as being not preferable because there is a possibility that it damages the desired charge characteristics.

the toner of the present invention, an inorganic fine powder may externally be added to the toner base particles as a fluidizing agent. As the fluidizing agent, fine powders of, e.g., silica, titanium oxide, alumina, double oxides of any of them, and any of these having been surface-treated may be used.

In the present invention, the toner may preferably have a weight-average particle diameter (D4) of from 3.0 μm to 15.0 μm, and much preferably from 4.0 μm to 12.0 μm, from the viewpoint of securing the stability of charging and obtaining images with high image quality.

The toner of the present invention may also preferably have a ratio of weight-average particle diameter D4 to number-average particle diameter D1 (hereinafter "weight-average particle diameter D4/number-average particle diameter D1" or "D4/D1"), of 1.35 or less, and much preferably 1.30 or less.

Incidentally, the weight-average particle diameter D4 and number-average particle diameter D1 of the toner of the present invention may differ in how to control them, depending on how to produce the toner particles. For example, in the case of suspension polymerization, they may be controlled by controlling the concentration of a dispersant used when an aqueous dispersion medium is prepared, the rate of reaction and stirring, the time for reaction and stirring, and so forth.

The toner particles in the present invention may be produced by using whatever method, and may preferably be obtained by a production process in which granulation is carried out in an aqueous medium, such as a suspension polymerization process or a suspension granulation process. Where toner particles are produced by any commonly available pulverization process, it involves a very high degree of technical difficulty in view of developing performance to add the wax component in a large quantity to toner particles. That the toner particles are obtained by granulation in an aqueous medium enables enclosure of the wax component in the particles, and can keep the wax component from coming exposed to the surfaces of toner particles even when the wax component is used in a large quantity.

The suspension polymerization process is one of the most preferable production processes in view of long-term developing stability in virtue of the enclosure of the wax component in the toner particles and in view of production cost such that any solvent is not used. Further, the particle shape of the toner is precisely controlled, and this enables enclosure of the colorant in individual toner particles in equal content. Hence, any effect on charge characteristics by the colorant can be uniform, and this brings a well balanced improvement in developing performance and transfer performance of the toner.

Meanwhile, the suspension granulation process does not have any heating step in its production steps. Hence, the resin and the wax component can be kept from coming compatibilized with each other, which may otherwise be compatibilized when a low-melting wax is used, thus the toner can be prevented from having a low glass transition temperature because of their coming compatibilized. In addition, the choices of toner materials making up the binder resin can be broad, and also it is easy to use as a chief component the polyester resin, which is commonly considered advantageous for fixing performance. Hence, this is a production process that is advantageous when a toner is produced which has resin composition to which the suspension polymerization process is not applicable.

In the case when the toner is produced by the suspension polymerization process, the polymeric compound of the present invention (or the polymerizable monomer of the present invention), the polymerizable monomer making up the binder resin, the colorant, the wax component, a polymerization initiator and so forth are mixed to prepare a polymerizable monomer composition, then the polymerizable monomer composition is dispersed in an aqueous medium to granulate the polymerizable monomer composition to form its particles, and thereafter polymerizing the polymerizable monomer in the particles of the polymerizable monomer composition to obtain toner particles. Here, it is preferable that the polymerizable monomer composition is a composition prepared by mixing a fluid dispersion obtained by dispersing the colorant in a first polymerizable monomer (or a portion of the polymerizable monomer), with at least a second polymerizable monomer (or the remaining polymerizable monomer). That is, the colorant is made to stand sufficiently dispersed in the first polymerizable monomer and thereafter the resultant fluid dispersion is mixed with the second polymerizable monomer together with the other toner materials. This can make the colorant present in the interior of the toner particles in a better dispersed state.

As the polymerization initiator used in the above suspension polymerization process, it may include known polymerization initiators, and may include, e.g., azo compounds, organic peroxides, inorganic peroxides, organometallic compounds and photopolymerization initiators. Stated more specifically, it may include azo type polymerization initiators such as 2,2'-azobis(isobutyronitrile), 2,2'-azobis(2-methylbutyronitrile), 2,2'-azobis(4-methoxy-2,4-dimethylvaleronitrile, 2,2'-azobis(2,4-dimethylvaleronitrile) and dimethyl 2,2'-azobis(isobutyrate); organic peroxide type polymerization initiators such as benzoyl peroxide, di-tert-butyl peroxide, tert-butyl peroxyisopropyl monocarbonate, tert-hexyl peroxybenzoate and tert-butyl peroxybenzoate; inorganic peroxide type polymerization initiators such as potassium persulfate and ammonium persulfate; and redox initiators such as a hydrogen peroxide-ferrous salt type, BPO-dimethylaniline type and a cerium(IV) salt-alcohol type. The photopolymerization initiator may include an acetophenone type, a benzoin ether type and a ketal type. Any of these polymerization initiators may be used in combination of two or more types.

The above polymerization initiator may preferably be in a concentration in the range of from 0.1 part by mass to 20 parts by mass, and much preferably from 0.1 part by mass to 10 parts by mass, based on 100 parts by mass of the polymerizable monomer. The polymerization initiator may a little vary in type depending on methods for polymerization, and may be used alone or in the form of a mixture, making reference to its 10-hour half-life period temperature.

The aqueous medium used in the suspension polymerization process may preferably be incorporated with a dispersion stabilizer. As the dispersion stabilizer, any known inorganic or organic dispersion stabilizer may be used. The inorganic dispersion stabilizer may include, e.g., calcium phosphate, magnesium phosphate, aluminum phosphate, zinc phosphate, magnesium carbonate, calcium carbonate, calcium hydroxide, magnesium hydroxide, aluminum hydroxide, calcium metasilicate, calcium sulfate, barium sulfate, bentonite, silica and alumina. The organic dispersion stabilizer may include, e.g., polyvinyl alcohol, gelatin, methyl cellulose, methyl hydroxypropyl cellulose, ethyl cellulose, carboxymethyl cellulose sodium salt, and starch.

A nonionic, anionic or cationic surface active agent may also be used as the dispersion stabilizer. For example, it may include sodium dodecyl sulfate, sodium tetradecyl sulfate, sodium pentadecyl sulfate, sodium octyl sulfate, sodium oleate, sodium laurate, potassium stearate, and calcium oleate.

Of the above dispersion stabilizers, it is preferable in the present invention to use an inorganic sparingly water-soluble dispersion stabilizer that is soluble in acids. Also, in the present invention, where an aqueous dispersion medium is prepared using the sparingly water-soluble dispersion stabilizer, such a dispersion stabilizer may preferably be used in such a proportion that it is in an amount ranging from 0.2 part by mass to 2.0 parts by mass based on 100 parts by mass of the polymerizable monomer. This is preferable in view of the stability of droplets in the aqueous dispersion medium of the polymerizable monomer composition. In the present invention, the aqueous dispersion medium may also preferably be prepared with use of water in an amount ranging from 300 parts by mass to 3,000 parts by mass based on 100 parts by mass of the polymerizable monomer composition.

In the present invention, where the aqueous dispersion medium in which the sparingly water-soluble inorganic dispersion stabilizer has been dispersed is prepared, it may be dispersed using a commercially available dispersion stabilizer as it is. In order to obtain particles of the dispersion stabilizer which have a fine and uniform particle size, the sparingly water-soluble inorganic dispersion stabilizer may be prepared by forming it in a liquid medium such as water with high-speed stirring. For example, where tricalcium phosphate is used as the dispersion stabilizer, an aqueous sodium phosphate solution and an aqueous calcium chloride solution may be mixed under high-speed stirring to form fine particles of the tricalcium phosphate, whereby a preferable dispersion stabilizer can be obtained.

In the case when the toner is produced by the suspension granulation process, the toner is produced in the following way, for example. First, the polymeric compound of the present invention, the binder resin, the colorant, the wax component and so forth are mixed in a solvent to prepare a solvent composition. Next, the solvent composition is dispersed in an aqueous medium to granulate the solvent composition to form its particles therein to obtain a toner particle suspension. Then, the suspension obtained is heated or put under reduced pressure to remove the solvent, thus toner particles can be obtained.

It is preferable that the solvent composition in the above step is a composition prepared by mixing a fluid dispersion obtained by dispersing the colorant in a first solvent, with a second solvent. That is, the colorant is more sufficiently dispersed in the first solvent and thereafter the resultant fluid dispersion is mixed with the second solvent together with the other toner materials. This can make the colorant present in the interior of the toner particles in a better dispersed state.

As the solvent used in the above suspension granulation process, it may include, e.g., hydrocarbons such as toluene, xylene and hexane; halogen-containing hydrocarbons such as methylene chloride, chloroform, dichloroethane, trichloroethane and carbon tetrachloride; alcohols such as methanol, ethanol, butanol and isopropyl alcohol; polyhydric alcohols such as ethylene glycol, propylene glycol, diethylene glycol and triethylene glycol; Cellosolves such as methyl Cellosolve and ethyl Cellosolve; ketones such as acetone, methyl ethyl ketone and methyl isobutyl ketone; ethers such as benzyl alcohol ethyl ether, benzyl alcohol isopropyl ether and tetrahydrofuran; and esters such as methyl acetate, ethyl acetate and butyl acetate. Any of these may be used alone or in the form of a mixture of two or more types. Of these, in order to readily remove the solvent in the toner particle suspension, it is preferable to use a solvent having a low boiling point and capable of dissolving the binder resin sufficiently.

The solvent may preferably be used in an amount ranging from 50 parts by mass to 5,000 parts by mass, and much preferably from 120 parts by mass to 1,000 parts by mass, based on 100 parts by mass of the binder resin.

The aqueous medium used in the suspension granulation process may preferably be incorporated with a dispersion stabilizer. As the dispersion stabilizer, any known inorganic or organic dispersion stabilizer may be used. The inorganic dispersion stabilizer may include calcium phosphate, calcium carbonate, aluminum hydroxide, calcium sulfate and barium carbonate. The organic dispersion stabilizer may include, e.g., water-soluble polymers such as polyvinyl alcohol, methyl cellulose, hydroxyethyl cellulose, ethyl cellulose, carboxymethyl cellulose sodium salt, sodium polyacrylate and sodium polymethacrylate; and surface active agents as exemplified by anionic surface active agents such as sodium dodecylbenzene sulfonate, sodium octadecyl sulfate, sodium oleate, sodium laurate and potassium stearate; cationic surface active agents such as laurylamine acetate, stearylamine acetate and lauryl trimethylammonium chloride; amphoteric surface active agents such as lauryl dimethylamine oxide; and nonionic surface active agents such as polyoxyethylene alkyl ethers, polyoxyethylene alkyl phenyl ethers and polyoxyethylene alkyl amines.

The dispersion stabilizer may be used in an amount ranging from 0.01 part by mass to 20 parts by mass based on 100 parts by mass of the binder resin.

Measuring methods and evaluation methods used in the present invention are described below.

(1) Compositional Analysis:

Structures of the polymerizable monomer and polymeric compound in the present invention are determined by using the following instrument.

$^{1}$H, $^{13}$C NMR:

Using ECA-400 (400 MHz), manufactured by JEOL Ltd.), measurement by nuclear magnetic resonance spectroscopy (NMR) is made at 25° C. in a deuterated solvent containing tetramethylsilane as an internal standard substance. The values of chemical shifts are shown as ppm shift values (δ values) assuming the value of the internal standard substance tetramethylsilane as 0.

MS:

Analysis by mass spectrometry is made using LC/MSD TOF, manufactured by Agilent Technologies Inc. Here, as ionization, electrospray ionization (ESI) is used.

(2) Measurement of Molecular Weight Distribution:

The molecular weight distribution of the polymeric compound in the present invention is measured by size exclusion chromatography (SEC), and calculated in terms of standard polystyrene. The measurement of molecular weight by SEC is made as shown below.

A sample is added to the following eluting solution in such a way as for the sample to be in a concentration of 1.0% by mass, and the solution obtained and having been left to stand at room temperature for 24 hours is filtered with a solvent-resistant membrane filter of 0.2 μm in pore diameter to make up a sample solution. The measurement is made under the following conditions.

Instrument: High-speed GPC HLC8220 GPC (manufactured by Tosoh Corporation).
Columns: Combination of two columns, ASAHIPAK GF-510HQ and GF-310HQ (available from Showa Denko K.K.).
Eluent: DMF (20 mmol/l, containing lithium bromide).
Flow rate: 0.6 ml/min.
Oven temperature: 40° C.
Amount of sample injected: 0.10 ml.

To calculate the molecular weight distribution of the sample, a molecular weight calibration curve is used which is prepared using a standard polystyrene resin (TSK Standard Polystyrene F-850, F-450, F-288, F-128, F-80, F-40, F-20, F-10, F-4, F-2, F-1, A-5000, A-2500, A-1000, A-500; available from Tosoh Corporation).

(3) Measurement of Acid Value:

The acid value of the polymeric compound in the present invention is determined in the following way.

Basic operation is made according to JIS K-0070.
1) A sample pulverized product is precisely weighed in an amount of from 0.5 g to 2.0 g. The mass at this point is represented by W (g).
2) The sample is put into a 300 ml beaker, and 150 ml of a toluene/ethanol (4/1) mixed solvent is added thereto to dissolve the sample.
3) Using an ethanol solution of 0.1 mol/l KOH, it is titrated by using a potential difference titration measuring instrument (e.g., an automatic titration measuring instrument COM-2500, manufacture by Hiranuma Sangyo Co., Ltd. may be used).
4) The amount of the KOH solution used at this point is represented by S (ml). A blank is measured simultaneously, and the amount of the KOH solution at this point is represented by B (ml).
5) The acid value is calculated according to the following expression. Here, f is the factor of the KOH solution.

$$\text{Acid value (mgKOH/g)} = \{(S-B) \times f \times 5.61\}/W.$$

(4) Evaluation of Charge Characteristics:

The charge characteristics of the polymeric compound in the present invention are evaluated by measuring charge quantity with a cascade type charge quantity measuring instrument manufactured by KYOCERA Chemical Corporation, on a coating film formed by coating a conductive substrate with the polymeric compound.

FIG. 1 is a diagrammatic view showing the charge quantity measuring instrument used in the present evaluation. In FIG. 1, reference numeral 11 denotes the conductive substrate; 12, a substrate holder stand; 13, the polymeric compound coating film; 14, a standard powder; 15, a standard powder feeder; 16, a standard powder receiver; and 17, an electrometer. A specific method of measurement by this instrument is as shown below.

1) The polymeric compound and, as a binder resin, polystyrene (weight-average molecular weight: 35,000, available from Sigma-Aldrich Corporation) are dissolved in methyl ethyl ketone, and the conductive substrate 11, made of aluminum, is coated by means of a wire bar with the solution obtained, followed by drying in an environment of 23° C./50% RH for 24 hours or more. At this stage, the amounts of the polymeric compound and binder resin are so controlled as to be in a proportion of 1:9 (in parts by mass). Also, the concentration of the coating solution and the type of the wire bar are so selected as for the coating film as to be 5 μm in layer thickness.

2) The conductive substrate 11 coated with the polymeric compound is attached to the substrate holder stand 12, and this substrate holder stand 12 is so fixed as for the conductive substrate 11 to be kept at an angle of inclination of 45°.

3) In an environment controlled at 23° C./50% RH and using as the standard powder 14 a manganese ferrite carrier (average particle diameter: 80 μm) available from Powdertech Co., the standard powder 14 is let flow from the standard powder feeder 15 over the polymeric compound coating film 13 at a flow rate of 15 g/min. Here, the flow path through which the standard powder 14 flows over the polymeric compound coating film 13 is kept so controlled as to be 20 mm in flow path length and 15 mm in flow path width.

4) The standard powder 14 having come into contact with the polymeric compound coating film 13 is electrostatically charged and then all collected in the standard powder receiver 16. The standard powder receiver 16 serves as Faraday cage, and the quantity of electric charges the standard powder 14 has received from the polymeric compound coating film 13 can be measured with the electrometer 17 connected. Meanwhile, the charge quantity of the polymeric compound coating film 13 is shown as an inverse sign of the charge quantity of the standard powder 14.

The charge characteristics of the polymeric compound are evaluated by the charge quantity the polymeric compound coating film 13 has when 50 g of the standard powder 14 is let flow over it in the above charge quantity measuring method, and are judged according to the following criteria.

A: Very good (the charge quantity of the polymeric compound coating film is less than −125 nC).
B: Good (the charge quantity of the polymeric compound coating film is −125 nC or more to less than −100 nC).
C: Feasible for practical use (the charge quantity of the polymeric compound coating film is −100 nC or more to less than −75 nC).
D: Infeasible for practical use (the charge quantity of the polymeric compound coating film is −75 nC or more). As long as the charge quantity of the polymeric compound coating film is less than −100 nC, the charge characteristics of the polymeric compound coating film are judged to be good.

(5) Evaluation of Developing Roller:

The developing roller incorporated in its surface layer with the charge control agent of the present invention is fitted to an evaluation-purpose copying machine (NP6035, manufactured by CANON INC.) making use of a positively chargeable toner, where stated images are continuously copied on 15,000 sheets in an environment controlled at temperature 30° C. and humidity 80% RH, and thereafter evaluation is made on fog and image density.

The evaluation on fog is made in the following way. Reflectance D1(%) at a solid white portion of a recording sheet on which images have been formed and reflectance D2(%) at a virgin portion of the same recording sheet are measured at 5 spots for each of these portions by using a white-light intensity meter TC-6DS/A, manufactured by Tokyo Denshoku Co., Ltd.), and an average value thereof is calculated. The value of D1 minus D2 is taken as fog density, which is judged according to the following criteria.
A: Very good (the fog density is less than 1.0%).
B: Good (the fog density is 1.0% or more to less than 1.5%).
C: Feasible for practical use (the fog density is 1.5% or more to less than 2.0%).
D: Inferior (the fog density is 2.0% or more).

As long as the fog density is less than 1.5%, the evaluation on fog is judged to be good.

The evaluation of image density is made in the following way. Reflection density at a solid black portion [OD(Bk)] of a recording sheet on which images have been formed is measured at 5 spots of that portion by using a reflection densitometer RD918, manufactured by Gretag Macbeth Ag., and an average value thereof is calculated. The evaluation of image density is judged according to the following criteria.
A: Very good (the reflection density is 1.4 or more).
B: Good (the reflection density is 1.3 or more to less than 1.4).
C: Feasible for practical use (the reflection density is 1.2 or more to less than 1.3).
D: Inferior (the reflection density is less than 1.2).

As long as the reflection density is 1.3 or more, the evaluation of image density is judged to be good.

(6) Measurement of Particle Size Distribution of Toner:

The weight-average particle diameter D4 and number-average particle diameter D1 of the toner are measured in the following way. COULTER MULTISIZER (manufactured by Beckman Coulter, Inc.) is used, and an interface (manufactured by Nikkaki Bios Co.) that outputs number distribution and volume distribution and a personal computer are connected. As an electrolytic solution, an aqueous 1% NaCl solution is prepared by using sodium chloride. For example, ISOTON R-II (available from Beckman Coulter, Inc.) may be used. Specific procedure for measurement is described in a catalogue of COULTER MULTISIZER (February, 2002 Edition) or an operation manual for the instrument, and is as shown below.

To 100 ml to 150 ml of the above aqueous electrolytic solution, 2 mg to 20 mg of a measuring sample (toner) is added. The electrolytic solution in which the sample has been suspended is subjected to dispersion treatment for about 1 to 3 minutes in an ultrasonic dispersion machine. The volume and number of toner particles with particle diameters of 2.0 µm or more to 64.0 µm or less are measured with the above COULTER MULTISIZER, using its 100 µm aperture. The data obtained are apportioned to 16 channels to determine the weight-average particle diameter D4, the number average particle diameter D1 and the value of D4/D1.

Figure 2:
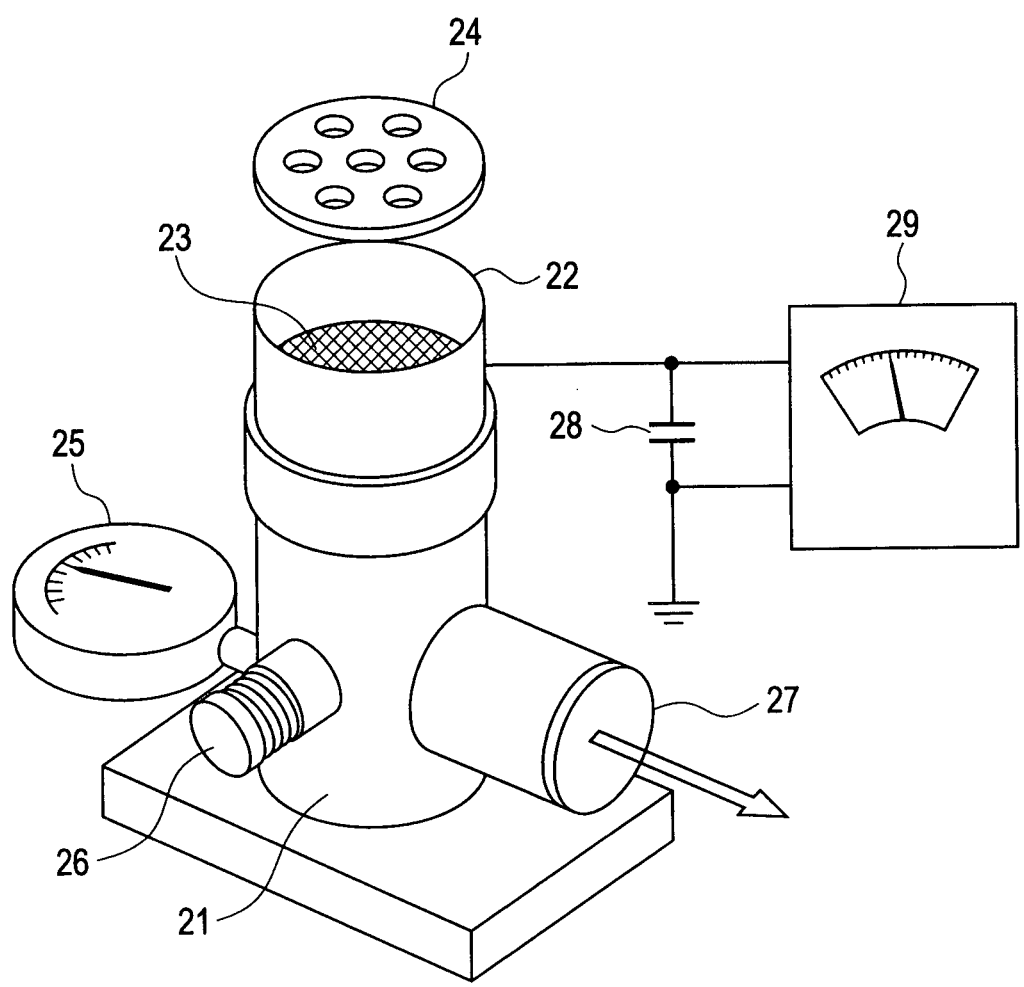
FIG. 2 is a view showing the construction of an instrument for measuring the triboelectric charge quantity of the toner of the present invention.

(7) Measurement of Charge Quantity of Toner:

To measure triboelectric charge quantity, 0.5 g of the toner and 9.5 g of a carrier are put into a 50 cc plastic container and then this is left to stand overnight in a normal temperature and normal humidity environment (23° C./50% RH). Thereafter, this is shaken for a stated time (10 seconds and 300 seconds each) at a shaking speed of 200 times per minute, and the triboelectric charge quantity of what has been thus shaken is measured with an instrument shown in FIG. 2.

About 0.3 g of the toner the triboelectric charge quantity of which is to be measured is put into a measuring container 22 made of a metal and to the bottom of which a conductive screen 23 of 500 meshes (mesh opening: 25 µm) is attached, and the container is covered with a lid 24 made of a metal. The total mass of the measuring container 22 at this point is expressed as W1 (g). Next, in a suction device 21 (made of an insulating material at least at the part coming into contact with the measuring container 22), air is sucked from a suction opening 27 and an air-flow control valve 26 is operated to control the pressure indicated by a vacuum indicator 25, to be −2.0 kPa (gauge pressure). In this state, suction is carried out for 2 minutes to remove the toner by suction. The potential indicated by an electrometer 29 at this point is expressed as V (volt). Here, reference numeral 28 denotes a capacitor, whose capacitance is expressed as C (µF). The total mass of the measuring container after the suction is expressed as W2 (g). The triboelectric charge quantity (µC/g) of this toner is calculated according to the following expression. Triboelectric charge quantity $(\mu C/g) = (C \times V)/(W1-W2)$.

The evaluation of charge quantity is judged according to the following criteria. In working examples, negatively chargeable toners are prepared.
A: Very good (the triboelectric charge quantity is −20.0 µC/g or less).
B: Good (the triboelectric charge quantity is −10.0 µC/g to −19.9 µC/g).
C: Feasible for practical use (the triboelectric charge quantity is −5.0 µC/g to −9.9 µC/g).
D: Inferior (the triboelectric charge quantity is −4.9 µC/g or more).

As long as the triboelectric charge quantity is −10.0 µC/g or less, the toner is judged to have good charge characteristics.

(8) Measurement of Reverse-Polarity Toner Quantity:

The reverse-polarity toner quantity (quantity of toner with reverse polarity) is measured with E-SPART Analyzer EST-3, manufactured by Hosokawa Micron Corporation, and the number of particles of reverse-polarity toner (positive-polarity toner) that is based on the total number of toner particles is measured. To make the measurement, 0.5 g of the toner and 9.5 g of a carrier are put into a 50 cc plastic container and then this is left to stand overnight in a normal temperature and normal humidity environment (23° C./50% RH). Thereafter, this is shaken for 5 minutes at a shaking speed of 200 times per minute, and the measurement is made on what has been thus shaken.

The evaluation on the reverse-polarity toner quantity is judged according to the following criteria.
A: Very good (any reverse-polarity toner is not present).
B: Good (the reverse-polarity toner is in a proportion of less than 5%).
C: Feasible for practical use (the reverse-polarity toner is in a proportion of 5% or more to less than 15%).
D: Inferior (the reverse-polarity toner is in a proportion of 15% or more).

As long as the reverse-polarity toner is in a proportion of less than 5%, the toner is judged to have good charge characteristics.

EXAMPLES

The present invention is described below in greater detail by giving working examples, to which, however, the present invention is by no means limited. In the working examples, "part(s)" as so termed refers to "part(s) by mass" in all occurrences.

Production of Polymerizable Monomer (a)

A polymerizable monomer (a) represented by the following structural formula was produced according to the following scheme.

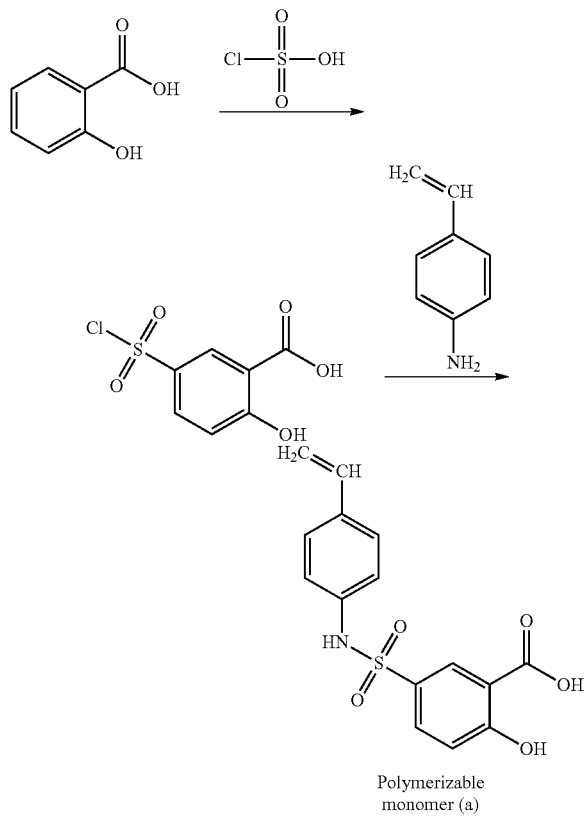

Polymerizable monomer (a)

Into a reaction vessel fitted with a cooling pipe, a stirrer, a thermometer and a nitrogen feed pipe, 100 parts of salicylic acid was fed, and then cooled to 15° C. or below. While the reaction solution obtained was kept at 15° C. or below, 438 parts of chlorosulfonic acid was slowly dropwise added thereto. After its addition made dropwise was completed, the reaction temperature was raised to 60° C., and the reaction was carried out at 60° C. for 2 hours. The resultant reaction solution was cooled to room temperature, and thereafter the reaction solution cooled was poured into 2,000 parts of crushed ice. The solid having come precipitated was separated by filtration, and then washed with ice water. The solid thus obtained was air-dried, and then re-crystallized with chloroform to obtain 90 parts of 5-chlorosulfonic acid (yield: 53%).

Into a reaction vessel fitted with a cooling pipe, a stirrer, a thermometer and a nitrogen feed pipe, 89 parts of the 5-chlorosulfonic acid and 120 parts of acetone were fed, which were dissolved therein, and thereafter the solution formed was cooled to 15° C. or below. While the reaction solution obtained was kept at 15° C. or below, a solution prepared by dissolving 47 parts of 4-aminostyrene in 40 parts of acetone was slowly dropwise added thereto. After its addition made dropwise was completed, the reaction solution was heated to 50° C., and the reaction was carried out at 50° C. until the 4-aminostyrene was completely utilized. After the reaction was completed, this reaction solution was cooled to room temperature, and then the solvent was evaporated off under reduced pressure. The residue obtained was dissolved in 350 parts of chloroform, followed by washing with 500 parts of 1 mol/liter hydrochloric acid and 500 parts of ion-exchanged water each. The organic phase formed was dried with sodium sulfate, and thereafter the solvent was evaporated off under reduced pressure. The residue obtained was purified by silica gel column chromatography to obtain 76 parts of the polymerizable monomer (a) (yield: 63%).

Figure 3:
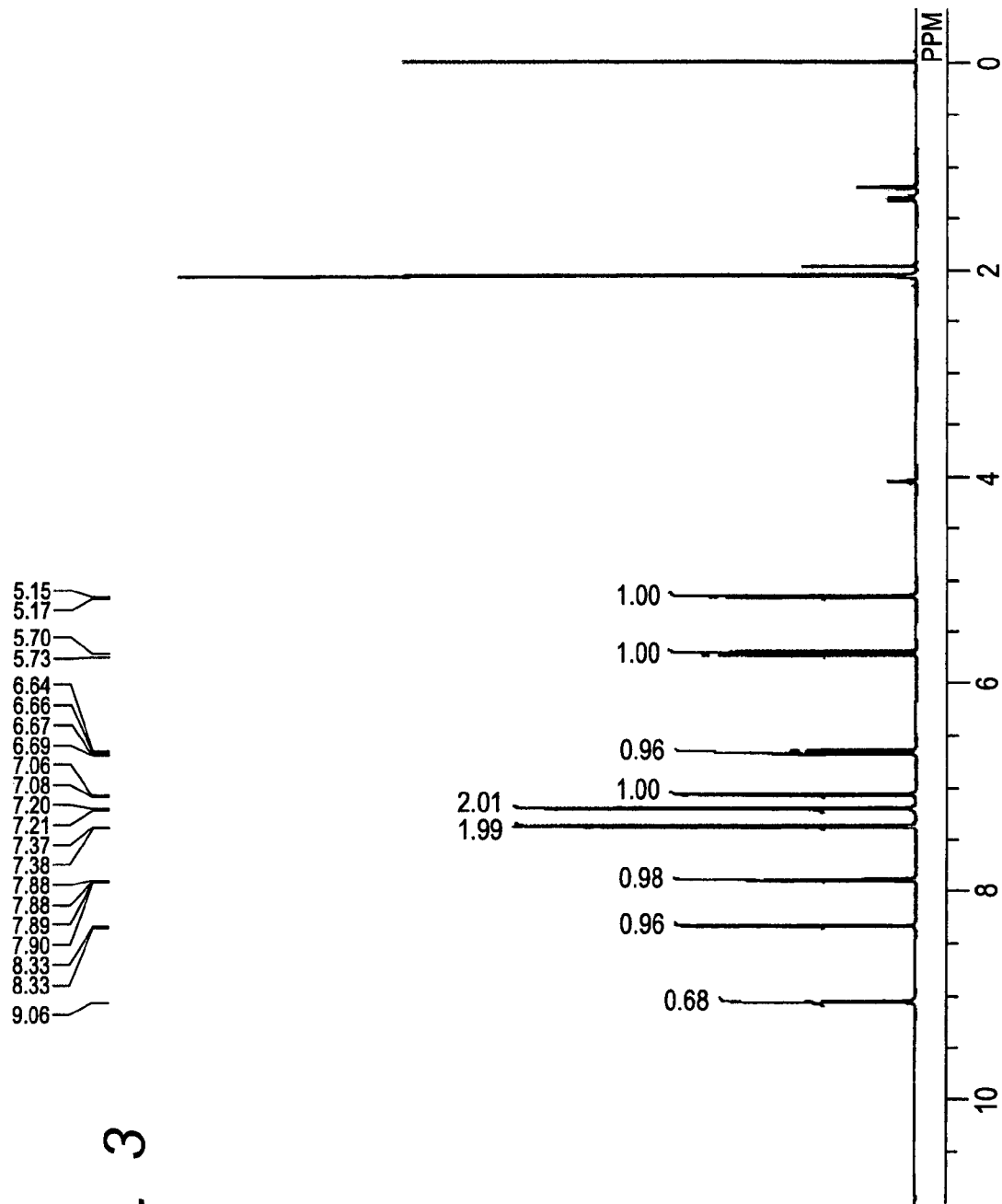
FIG. 3 is a $^1$H NMR spectrum chart of a polymerizable monomer (a) of the present invention.

That the polymerizable monomer (a) obtained had the structure represented by the above formula was identified by the instrumental analysis described previously. The results of analysis are shown below. A $^1$H NMR spectrum chart of the polymerizable monomer (a) is also shown in FIG. 3.

Results of $^1$H NMR (400 MHz, in deuterated acetone, 25° C.) (see FIG. 3):

δ[ppm] 9.06 (1H, s), 8.33 (1H, d), 7.89 (1H, dd), 7.38 (1H, d), 7.20 (1H, d), 7.07 (1H, d), 6.66 (1H, dd), 5.71 (1H, d), 5.16 (1H, d).

Results of $^{13}$C NMR (100 MHz, in deuterated acetone, 25° C.):

δ[ppm] 171.6, 165.9, 138.2, 136.9, 135.1, 135.0, 131.4, 131.2, 127.9, 121.9, 119.1, 113.7, 113.3.

Results of MS (ESI-TOF):

m/z 318.0434 ([M-H]$^-$).

Production of Polymerizable Monomer (b)

A polymerizable monomer (b) was produced in the same way as Production of Polymerizable Monomer (a) except that 55 parts of 4-methylsalicylic acid was used in place of the salicylic acid.

Production of Polymerizable Monomer (c)

A polymerizable monomer (c) was produced in the same way as Production of Polymerizable Monomer (a) except that 55 parts of 3-methylsalicylic acid was used in place of the salicylic acid.

Production of Polymerizable Monomer (d)

A polymerizable monomer (d) was produced in the same way as Production of Polymerizable Monomer (a) except that 62 parts of 4-chlorosalicylic acid was used in place of the salicylic acid.

Production of Polymerizable Monomer (e)

A polymerizable monomer (e) was produced in the same way as Production of Polymerizable Monomer (a) except that 56 parts of 2,3-dihydroxybenzoic acid was used in place of the salicylic acid.

Production of Polymerizable Monomer (f)

A polymerizable monomer (f) was produced in the same way as Production of Polymerizable Monomer (a) except that 61 parts of 3-methoxysalicylic acid was used in place of the salicylic acid.

Production of Polymerizable Monomer (g)

A polymerizable monomer (g) was produced in the same way as Production of Polymerizable Monomer (a) except that 70 parts of 3-hydroxy-2-p-cymenecaroxylic acid was used in place of the salicylic acid.

Production of Polymerizable Monomer (h)

A polymerizable monomer (h) was produced in the same way as Production of Polymerizable Monomer (a) except that 68 parts of 1-hydroxy-2-naphthoic acid was used in place of the salicylic acid.

Production of Polymerizable Monomer (i)

A polymerizable monomer (i) was produced in the same way as Production of Polymerizable Monomer (a) except that 3-aminostyrene was used in place of the 4-aminostyrene.

Production of Polymerizable Monomer (j)

A polymerizable monomer (j) was produced in the same way as Production of Polymerizable Monomer (a) except that 28 parts of acrylamide was used in place of the 4-aminostyrene.

Production of Polymerizable Monomer (k)

A polymerizable monomer (k represented by the following structural formula was produced according to the following scheme.

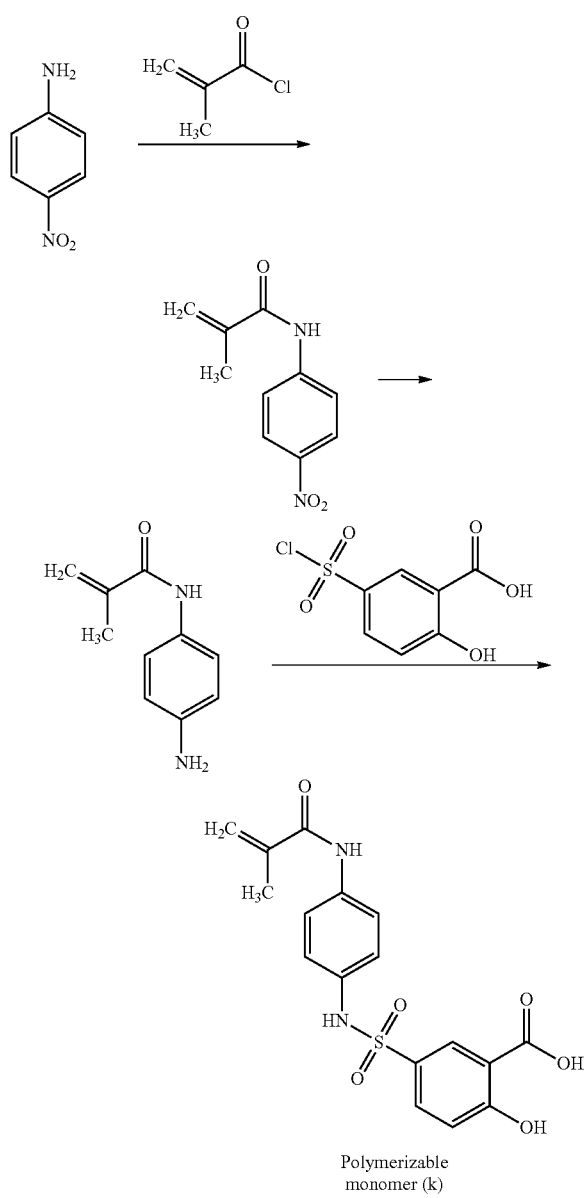

Polymerizable monomer (k)

Into a reaction vessel fitted with a cooling pipe, a stirrer, a thermometer and a nitrogen feed pipe, 50 parts of 4-nitroaniline, 40 parts of triethylamine and 525 parts of chloroform were fed, and then cooled to 5° C. or below. While the reaction solution obtained was kept at 5° C. or below, a solution prepared by dissolving 41 parts of methacrylic acid chloride in 30 parts of chloroform was dropwise added thereto. After its addition made dropwise was completed, the reaction solution was heated to room temperature, and, as it was, the reaction was carried out for 4 hours. After the reaction was completed, the organic phase formed was washed with 200 parts of ion-exchanged water. This organic phase was then dried with sodium sulfate, and thereafter the solvent was evaporated off under reduced pressure. The residue obtained was purified by silica gel column chromatography to obtain 22 parts of an intermediate N-(4-nitrophenyl)methacrylamide (yield: 31%).

Into a reaction vessel fitted with a cooling pipe, a stirrer, a thermometer and a nitrogen feed pipe, 20 parts of the N-(4-nitrophenyl)methacrylamide and 315 parts of ethanol were fed, which were dissolved therein, and thereafter the solution formed was cooled to 0° C. While the reaction solution obtained was kept at 0° C., 65 parts of tin(II) chloride was dividedly added thereto. After its addition was completed, the reaction solution was heated to room temperature, and, as it was, the reaction was carried out for 20 hours. After the reaction was completed, the solvent was evaporated off under reduced pressure, then 200 parts of ion-exchanged water was added to the reaction solution, and its pH was adjusted to 7 with use of an aqueous 12 mol/liter sodium hydroxide solution. To the solid having come precipitated, 200 parts of ethyl acetate was added, and insoluble matter was separated by filtration. The filtrate obtained was washed with 200 parts of ion-exchanged water, which was then dried with sodium sulfate, and thereafter the solvent was evaporated off under reduced pressure. The residue obtained was purified by silica gel column chromatography to obtain 12 parts of an intermediate N-(4-aminophenyl)methacrylamide (yield: 71%).

Into a reaction vessel fitted with a cooling pipe, a stirrer, a thermometer and a nitrogen feed pipe, 10 parts of the N-(4-aminophenyl)methacrylamide, 6 parts of triethylamine and 79 parts of acetone were fed, and then cooled to 15° C. or below. While the reaction solution obtained was kept at 15° C. or below, a solution prepared by dissolving 10 parts of 5-chlorosulfonic acid in 40 parts of acetone was dropwise added thereto. After its addition made dropwise was completed, the reaction solution was heated to room temperature, and, as it was, the reaction was carried out for 20 hours. After the reaction was completed, the solvent was evaporated off under reduced pressure, and the residue obtained was dissolved in 100 parts of ethyl acetate. The organic phase formed was washed with 50 parts of 1 mol/liter hydrochloric acid and 50 parts of ion-exchanged water each, followed by drying with sodium sulfate, and thereafter the solvent was evaporated off under reduced pressure. The residue obtained was purified by silica gel column chromatography to obtain 7 parts of the polymerizable monomer (k) (yield: 53%).

Figure 4:
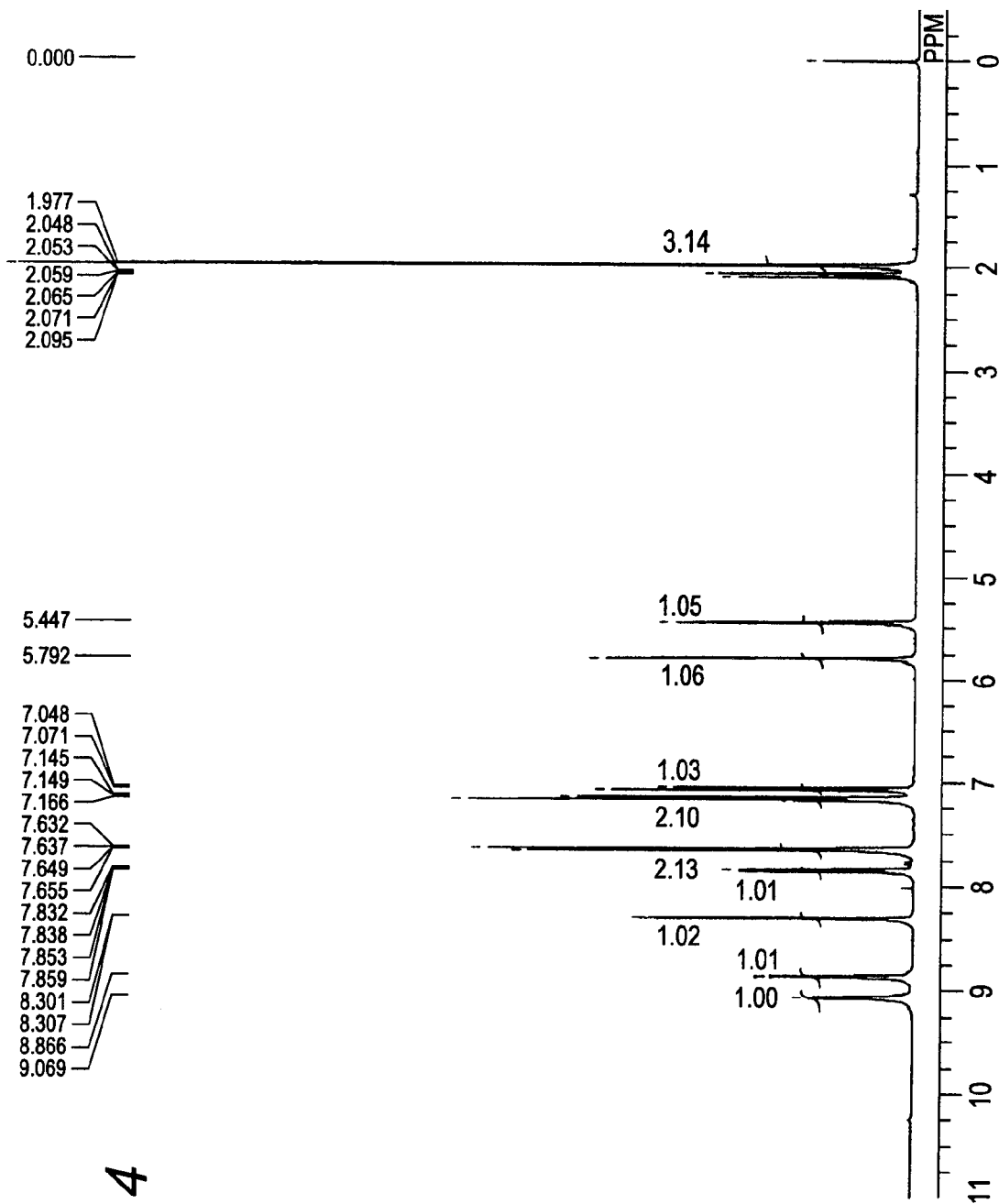
FIG. 4 is a $^1$H NMR spectrum chart of a polymerizable monomer (k) of the present invention.

That the polymerizable monomer (k) obtained had the structure represented by the above formula was identified by the instrumental analysis described previously. The results of analysis are shown below. A $^1$H NMR spectrum chart of the polymerizable monomer (k) is also shown in FIG. 4.

Results of $^1$H NMR (400 MHz, in deuterated acetone, 25° C.) (see FIG. 4):

δ[ppm] 11.45 (1H, br), 9.07 (1H, d), 8.87 (1H, s), 8.31 (1H, s), 7.85 (1H, dd), 7.64 (2H, d), 7.16 (2H, d), 7.06 (1H, d), 5.79 (1H, s), 5.45 (1H, s), 1.98 (3H, s).

Results of $^{13}$C NMR (100 MHz, in deuterated acetone, 25° C.):

δ[ppm] 171.6, 167.3, 165.8, 141.9, 137.4, 135.0, 133.8, 131.2, 123.2, 121.5, 119.8, 118.9, 113.2, 18.9.

Results of MS (ESI-TOF):

m/z 375.3759 ([M-H]$^-$).

Production of Polymeric Compound A

Into a reaction vessel fitted with a cooling pipe, a stirrer, a thermometer and a nitrogen feed pipe, the following materials were fed, and nitrogen bubbling was carried out for 30 minutes.

| | |
|---|---|
| Styrene | 100 parts |
| Polymerizable monomer (a) | 19.6 parts |
| Tert-butyl peroxyisopropyl carbonate (PERBUTYL I-75, trade name; available from | 7.2 parts |

NOF Corporation)
Propylene glycol monomethyl ether acetate     290.0 parts

The reaction mixture of these was heated at 145° C. for 8 hours in an atmosphere of nitrogen to complete polymerization reaction. The reaction solution obtained was cooled to room temperature, and thereafter the solvent was evaporated off under reduced pressure. The solid obtained was re-precipitated twice with acetone-methanol, followed by drying under reduced pressure at 50° C. and 0.1 kPa or less to obtain a polymeric compound A.

Figure 5:
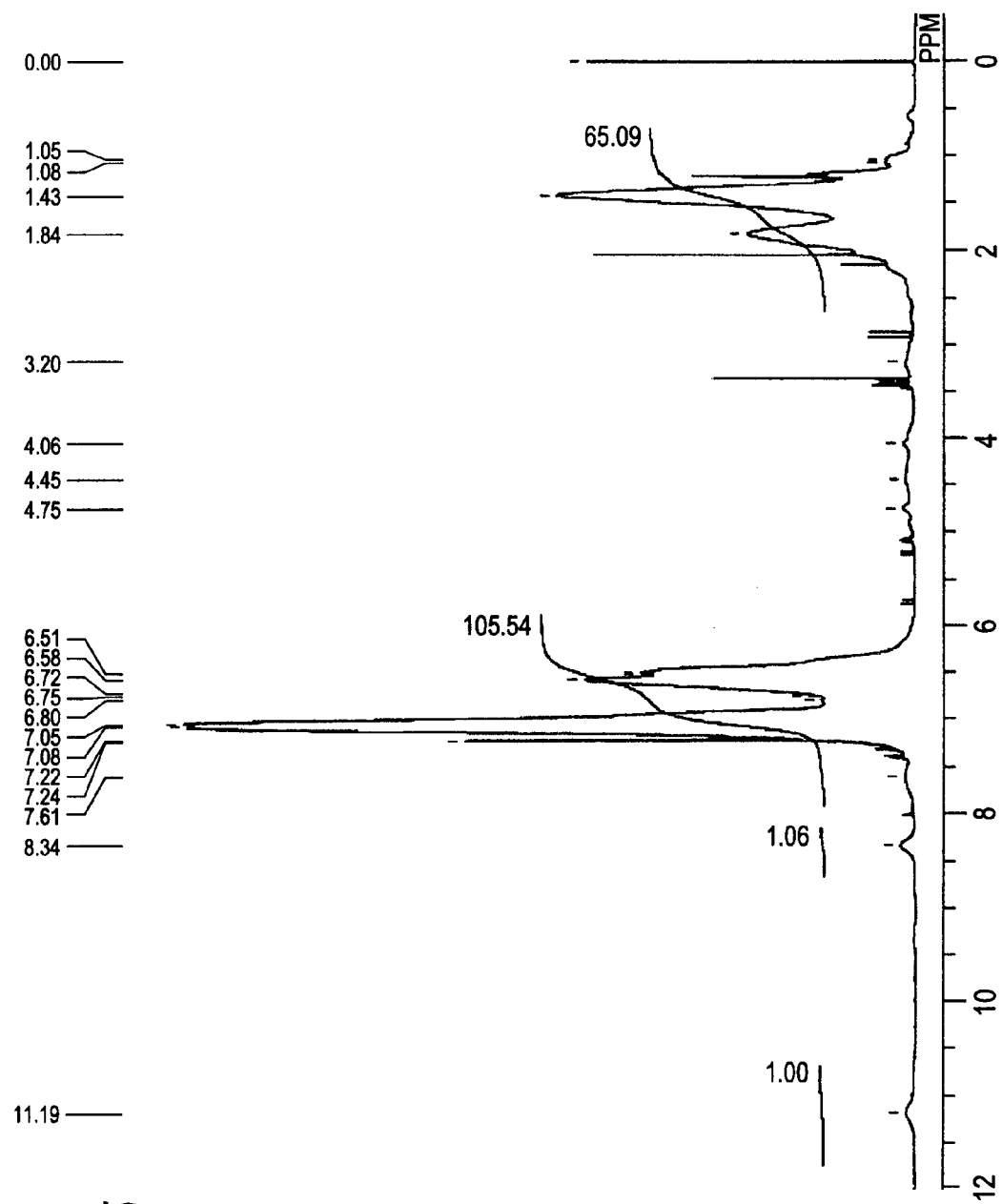
FIG. 5 is a $^1$H NMR spectrum chart of a polymeric compound A of the present invention.

The polymeric compound A obtained was analyzed by the analytical method described previously. The results are shown below. In the following, "St" in NMR analysis stands for a signal due to a styrene unit, and "a" a signal due to the polymerizable monomer (a). A $^1$H NMR spectrum chart of the polymeric compound A is also shown in FIG. 5.

Molecular weight: Weight-average molecular weight (Mw) of 15,400.

Results of $^1$H NMR (400 MHz, in deuterated chloroform, 25° C.)(see FIG. 5):

δ[ppm] 11.19(a), 8.34(a), 7.4-6.2(St,a), 2.5-1.0(St,a).

Acid value: 26.0 mgKOH/g.

From the above results, it was identified that the polymeric compound A had therein the unit of the polymerizable monomer (a) in a content of 5 mol %.

Production of Polymeric Compound B

A polymeric compound B was produced in the same way as Production of Polymeric Compound A except that the polymerizable monomer (a) was used in an amount of 39.2 parts.

Production of Polymeric Compound C

A polymeric compound C was produced in the same way as Production of Polymeric Compound A except that 20.4 parts of the polymerizable monomer (b) was used in place of the polymerizable monomer (a).

Production of Polymeric Compound D

A polymeric compound D was produced in the same way as Production of Polymeric Compound A except that 20.4 parts of the polymerizable monomer (c) was used in place of the polymerizable monomer (a).

Production of Polymeric Compound E

A polymeric compound E was produced in the same way as Production of Polymeric Compound A except that 21.7 parts of the polymerizable monomer (d) was used in place of the polymerizable monomer (a).

Production of Polymeric Compound F

A polymeric compound F was produced in the same way as Production of Polymeric Compound A except that 20.6 parts of the polymerizable monomer (e) was used in place of the polymerizable monomer (a).

Production of Polymeric Compound G

A polymeric compound G was produced in the same way as Production of Polymeric Compound A except that 21.4 parts of the polymerizable monomer (f) was used in place of the polymerizable monomer (a).

Production of Polymeric Compound H

A polymeric compound H was produced in the same way as Production of Polymeric Compound A except that 23.0 parts of the polymerizable monomer (g) was used in place of the polymerizable monomer (a).

Production of Polymeric Compound I

A polymeric compound I was produced in the same way as Production of Polymeric Compound A except that 22.7 parts of the polymerizable monomer (h) was used in place of the polymerizable monomer (a).

Production of Polymeric Compound J

A polymeric compound J was produced in the same way as Production of Polymeric Compound A except that 19.6 parts of the polymerizable monomer (i) was used in place of the polymerizable monomer (a).

Production of Polymeric Compound K

A polymeric compound K was produced in the same way as Production of Polymeric Compound A except that 16.7 parts of the polymerizable monomer (j) was used in place of the polymerizable monomer (a).

Production of Polymeric Compound L

A polymeric compound L was produced in the same way as Production of Polymeric Compound A except that 23.1 parts of the polymerizable monomer (k) was used in place of the polymerizable monomer (a).

Production of Polymeric Compound M

A polymeric compound M was produced in the same way as Production of Polymeric Compound A except that the materials to be fed were formulated as shown below.

| | |
|---|---|
| Styrene | 100 parts |
| Polymerizable monomer (a) | 19.6 parts |
| Acrylic acid | 3.9 parts |
| Tert-butyl peroxyisopropyl carbonate (PERBUTYL I-75, trade name; available from NOF Corporation) | 7.2 parts |
| Propylene glycol monomethyl ether acetate | 290.0 parts |

Production of Polymeric Compound N

A polymeric compound N was produced in the same way as Production of Polymeric Compound M except that 6.9 parts of n-butyl acrylate was used in place of the acrylic acid.

Production of Polymeric Compound O

A polymeric compound O was produced in the same way as Production of Polymeric Compound M except that 113.5 parts of α-methylstyrene was used in place of the styrene and 7.6 parts of n-butyl methacrylate was used in place of the acrylic acid.

Production of Polymeric Compound P

A polymeric compound P was produced in the same way as Production of Polymeric Compound M except that 6.8 parts of N,N'-diethylacrylamide was used in place of the acrylic acid.

Production of Polymeric Compound Q for Comparison

A polymeric compound Q for comparison was produced in the same way as Production of Polymeric Compound A except that 11.1 parts of 2-acrylamido-2-methylpropanesulfonic acid was used in place of the polymerizable monomer (a).

Production of Polymeric Compound R for Comparison

A polymeric compound R for comparison was produced in the same way as Production of Polymeric Compound A except that 9.9 parts of 5-vinylsalicylic acid was used in place of the polymerizable monomer (a).

About the polymeric compounds A to R produced as described above, their compositional ratios calculated from $^1$H NMR analysis, acid values and weight-average molecular weights (Mw) were measured by the methods described previously. The results are shown in Table 1.

TABLE 1

Composition & Physical Properties of Polymeric Compound

| Polymeric compound | Polymerizable monomer | \multicolumn{5}{c}{Copolymer components I} | II | III | Compositional ratio (molar ratio) I:II:III | Acid value (mg-KOH/g) | Mw |
|---|---|---|---|---|---|---|---|---|---|---|---|
| | | $R_1$ | $R_2$ | $R_3$ | $R_4$ | A | | | | | |
| A | (a) | H | H | H | H | X—C6H4—Y (para) | styrene | none | 5:95:0 | 26.0 | 15,400 |
| B | (a) | H | H | H | H | X—C6H4—Y (para) | styrene | none | 10:90:0 | 50.3 | 13,600 |
| C | (b) | H | H | $CH_3$ | H | X—C6H4—Y (para) | styrene | none | 5:95:0 | 24.8 | 14,700 |
| D | (c) | H | H | H | $CH_3$ | X—C6H4—Y (para) | styrene | none | 5:95:0 | 25.2 | 17,300 |
| E | (d) | H | H | Cl | H | X—C6H4—Y (para) | styrene | none | 5:95:0 | 23.4 | 16,800 |
| F | (e) | H | H | H | OH | X—C6H4—Y (para) | styrene | none | 5:95:0 | 27.9 | 15,600 |
| G | (f) | H | H | H | $OCH_3$ | X—C6H4—Y (para) | styrene | none | 5:95:0 | 26.3 | 12,900 |
| H | (g) | H | $CH_3$ | H | $CH(CH_3)_2$ | X—C6H4—Y (para) | styrene | none | 5:95:0 | 23.9 | 14,500 |
| I | (h) | H | H | —$C_2H_4$— | | X—C6H4—Y (para) | styrene | none | 5:95:0 | 26.1 | 18,100 |
| J | (i) | H | H | H | H | X—C6H4—Y (meta) | styrene | none | 5:95:0 | 24.7 | 17,000 |
| K | (j) | H | H | H | H | X—C(=O)—Y | styrene | none | 5:95:0 | 26.4 | 13,500 |

TABLE 1-continued

Composition & Physical Properties of Polymeric Compound

| Polymeric compound | Polymerizable monomer | $R_1$ | $R_2$ | $R_3$ | $R_4$ | A | II | III | Compositional ratio (molar ratio) I:II:III | Acid value (mg-KOH/g) | Mw |
|---|---|---|---|---|---|---|---|---|---|---|---|
| L | (k) | $CH_3$ | H | H | H | X—C(=O)—NH—C$_6$H$_4$—Y | styrene | none | 5:95:0 | 24.0 | 16,800 |
| M | (a) | H | H | H | H | X—C$_6$H$_4$—Y | styrene | acrylic acid | 5:90:5 | 48.7 | 15,500 |
| N | (a) | H | H | H | H | X—C$_6$H$_4$—Y | styrene | n-butyl acrylate | 5:90:5 | 23.6 | 12,300 |
| O | (a) | H | H | H | H | X—C$_6$H$_4$—Y | α-methyl styrene | n-butyl methacrylate | 5:90:5 | 24.4 | 13,900 |
| P | (a) | H | H | H | H | X—C$_6$H$_4$—Y | styrene | N,N'-diethyl acryl-amide | 5:90:5 | 26.5 | 18,300 |
| Q | 2-acrylamido-2-methylpropanesulfonic acid | | | | | | styrene | None | 5:95:0 | 22.9 | 13,500 |
| R | 5-vinylsalicylic acid | | | | | | styrene | None | 5:95:0 | 27.1 | 15,500 |

[In Table 1, "Copolymer component I" indicates the polymerizable monomer of the present invention, used in synthesizing the polymeric compound. "R1" to "R4" are R1 to R4 in the general formula (1). In regard to the linking group "A", "X" is the bonding position on the carbon atom side and "Y" is the bonding position on the nitrogen atom side.]

Roller Example 1

Production of Developing Roller 1
Surface Layer Composition Preparing Step:
  What was composed as shown below were put to dispersion for 3 hours by means of a ball mill.

| | |
|---|---|
| Urethane coating material (NIPPOLAN N5033, trade name; available from Nippon Polyurethane Industry Co., Ltd.) | 100 parts |
| Polymeric compound A | 10 parts |
| Carbon black (TOKA BLACK #7360SB, trade name; available from Tokai Carbon Co., Ltd.) | 50 parts |
| Urethane particles (ART PEARL C400, trade name; available from Negami Kogyo K.K.; average particle diameter: 15 μm) | 6 parts |
| Methyl ethyl ketone | 1,000 parts |

To the fluid dispersion obtained, 10 parts of a modified tolylene diisocyanate (COLONATE L, trade name; available from Nippon Polyurethane Industry Co., Ltd.) was added as a curing agent to make up a surface layer composition.

Elastic Layer Forming Step:
  A mandrel (made of stainless steel) of 8 mm in outer diameter was concentrically set in a cylindrical mold of 16 mm in inner diameter, and, as a material for a conductive elastic layer, liquid conductive silicone rubber (available from Dow Corning Toray Silicone Co., Ltd.; Asker-C hardness: 35 degrees; volume resistivity: $10 \times 10^9$ Ω·cm) was casted into it. Thereafter, this was heated for 20 minutes in a 130° C. oven to carry out molding. After demolding, the molded product was subjected to secondary vulcanization for 4 hours in a 200° C. oven to obtain a roller with an elastic layer formed thereon (layer thickness: 4 mm).

Surface Layer Forming Step:
  While the above surface layer composition was stirred, the roller with the elastic layer thus formed was so coated thereon with the surface layer composition by dipping as to form a surface layer in a layer thickness of 20 μm. The wet coating formed was dried for 15 minutes in a 80° C. oven, followed by curing for 4 hours in a 140° C. oven to obtain a developing roller 1.

Roller Examples 2 to 16

Production of Developing Rollers 2 to 16
  Developing rollers 2 to 16 were produced in the same way as Production of Developing Roller 1 except that the polymeric compounds B to P, respectively, were used in place of the polymeric compound A.

Comparative Roller Example 1

Production of Developing Roller 17

A developing roller 17 for comparison was produced in the same way as Production of Developing Roller 1 except that the polymeric compound A was not added to the surface layer composition.

Comparative Roller Example 2

Production of Developing Roller 18

A developing roller 18 for comparison was produced in the same way as Production of Developing Roller 1 except that in the surface layer composition a salicylic acid aluminum complex (BONTRON E-108, trade name; available from Orient Chemical Industries, Ltd.) was used in place of the polymeric compound A.

Comparative Roller Examples 3 & 4

Production of Developing Rollers 19 and 20

Developing rollers 19 and 20 for comparison was produced in the same way as Production of Developing Roller 1 except that in the surface layer composition the polymeric compounds Q and R, respectively, were used in place of the polymeric compound A.

The evaluation of charge characteristics of the polymeric compounds produced as described above and the evaluation on fog and image density in forming images by using the respective developing rollers were made by the methods described previously. The results are shown in Table 2.

TABLE 2

Evaluation of Polymeric Compound & Developing Roller

| Developing roller No. | Polymeric compound Type | Charge characteristics | Fog | Image density |
|---|---|---|---|---|
| Roller Example: | | | | |
| 1 | 1 | Polymeric compound A | A | A | A |
| 2 | 2 | Polymeric compound B | A | A | A |
| 3 | 3 | Polymeric compound C | A | A | A |
| 4 | 4 | Polymeric compound D | A | A | A |
| 5 | 5 | Polymeric compound E | A | A | A |
| 6 | 6 | Polymeric compound F | A | B | A |
| 7 | 7 | Polymeric compound G | A | A | A |
| 8 | 8 | Polymeric compound H | A | A | A |
| 9 | 9 | Polymeric compound I | A | A | A |
| 10 | 10 | Polymeric compound J | A | A | A |
| 11 | 11 | Polymeric compound K | A | A | A |
| 12 | 12 | Polymeric compound L | A | A | A |
| 13 | 13 | Polymeric compound M | A | B | B |
| 14 | 14 | Polymeric compound N | A | A | A |
| 15 | 15 | Polymeric compound O | A | A | A |
| 16 | 16 | Polymeric compound P | B | B | B |
| Comparative Roller Example: | | | | |
| 1 | 17 | none | D | D | D |
| 2 | 18 | salicylic acid aluminum complex | C | C | D |
| 3 | 19 | Polymeric compound Q | C | C | C |
| 4 | 20 | Polymeric compound R | B | C | C |

As can be seen from Table 2, it has been ascertained that the polymeric compound of the present invention has superior charge characteristics and that the use of the developing roller to the surface layer of which the polymeric compound of the present invention is added enables images to be obtained which have high image density and less fog.

Toner Example 1

Production of Toner 1
Polymerizable Monomer Composition Preparing Step:
What was composed as shown below was mixed and thereafter put to dispersion for 3 hours by means of a ball mill.

| | |
|---|---|
| Styrene | 82.0 parts |
| 2-Ethylhexyl acrylate | 18.0 parts |
| Divinylbenzene | 0.1 part |
| C.I. Pigment Blue 15:3 | 5.5 parts |
| Polyester resin (polycondensation product of propylene oxide modified bisphenol A with isophthalic acid; glass transition point: 65° C.; weight-average molecular weight (Mw): 10,000; number-average molecular weight (Mn): 6,000) | 5.0 parts |
| Polymeric compound A | 1.0 parts |

The fluid dispersion obtained was heated to 60° C. with stirring at 300 rpm, and thereafter 12.0 parts of ester wax (peak temperature of maximum endothermic peak in DSC measurement: 70° C.; number-average molecular weight (Mn): 704) and 3.0 parts of 2,2'-azobis(2,4-dimethylvaleronitrile) were added thereto to make up a polymerizable monomer composition.

Dispersion Stabilizer Preparing Step:

Into a 2-liter four-necked flask fitted with a high-speed stirrer TK-homomixer (manufactured by PRIMIX Corporation), 710 parts of ion-exchanged water and 450 parts of an aqueous 0.1 mol/liter sodium phosphate solution were introduced, and these were heated to 60° C. with stirring at 12,000 rpm. To the mixture obtained, 68.0 parts of an aqueous 1.0 mol/liter calcium chloride solution was slowly added to prepare an aqueous dispersion medium containing calcium chloride as a fine slightly water-soluble dispersion stabilizer.

Granulation and Polymerization Step:

Into the aqueous dispersion medium obtained, the above polymerizable monomer composition was introduced to carry out granulation for 15 minutes while keeping a number of revolutions of 12,000 rpm. Thereafter, the high-speed stirrer was changed for a stirrer having propeller stirring blades, and, at its internal temperature of 60° C., the polymerization was continued for 5 hours. Thereafter, the internal temperature was raised to 80° C., and the polymerization was further continued for 3 hours. After the polymerization was completed, residual monomers were evaporated off at 80° C. under reduced pressure, followed by cooling to 30° C. to obtain a fine polymer particle fluid dispersion.

Washing and Drying Steps:

The fine polymer particle fluid dispersion obtained was moved to a washing container, and diluted hydrochloric acid was added thereto with stirring to make adjustment of pH to 1.5. The resultant fluid dispersion was stirred for 2 hours, followed by solid-liquid separation by means of a filter to obtain fine polymer particles. This was introduced into 1.0 liter of ion-exchanged water and stirred to make up a fluid dispersion again, followed by solid-liquid separation by means of the filter. This operation was carried out three times, and thereafter the fine polymer particles having finally been obtained by solid-liquid separation were sufficiently dried by means of a 30° C. dryer to obtain toner particles.

External Addition Step:

In 100.0 parts of the toner particles (toner base particles) obtained, 1.0 part of hydrophobic fine silica powder (number-average particle diameter of primary particles: 7 nm) having been surface-treated with hexamethyldisilazane, 0.15 part of fine rutile titanium oxide powder (number-average particle diameter of primary particles: 45 nm) and 0.5 part of fine rutile titanium oxide powder (number-average particle diameter of primary particles: 200 nm) were dry-process mixed for 5 minutes by means of Henschel mixer (manufactured by Nippon Coke & Engineering Co., Ltd.) to obtain a toner 1.

Toner Examples 2 to 16

Production of Toners 2 to 16

Toners 2 to 16 were produced in the same way as Toner Example 1 except that the polymeric compounds B to P, respectively, were used in place of the polymeric compound A.

Toner Example 17

Production of Toner 17
Mixing Step:

What was composed as shown below was put to dispersion for 24 hours by means of a ball mill to obtain 200 parts of a toner composition liquid mixture.

| | |
|---|---|
| Ethyl acetate | 100.0 parts |
| C.I. Pigment Blue 15:3 | 5.0 parts |
| Polar resin | 85.0 parts |
| (saturated polyester, polycondensation product of propylene oxide modified bisphenol A with phthalic acid; glass transition point Tg: 75.9° C.; weight-average molecular weight Mw: 11,000; number-average molecular weight Mn: 4,200; acid value: 11 mgKOH/g) | |
| Hydrocarbon wax | 9.0 parts |
| (Fischer-Tropsch wax; peak temperature of maximum endothermic peak in DSC measurement: 80° C.; weight-average molecular weight Mw: 750) | |
| Polymeric compound A | 1.0 part |

Dispersion Suspension Step:

What was composed as shown below was put to dispersion for 24 hours by means of a ball mill to dissolve carboxymethyl cellulose to obtain an aqueous medium.

| | |
|---|---|
| Calcium carbonate | 20.0 parts |
| (coated with acrylic-acid type copolymer) | |
| Carboxymethyl cellulose | 0.5 part |
| (trade name: CELLOGEN BS-H, available from Dai-ichi Kogyo Seiyaku Co., Ltd.) | |
| Ion-exchanged water | 99.5 parts |

1,200 parts of the aqueous medium obtained was put into TK-homomixer, and stirred rotating a rotating blade at a peripheral speed of 20 m/sec, during which 1,000 parts of the above toner composition fluid mixture was introduced thereinto. These were stirred for 1 minute while keeping temperature constantly at 25° C., to obtain a suspension.

Solvent Removal Step:

2,200 g of the suspension obtained in the dispersion suspension step was stirred by means of Full-zone blade (manufactured by Kobelco Eco-Solutions Co., Ltd.) at a peripheral speed of 45 m/min, during which, keeping the temperature constantly at 40° C., the gaseous phase on the suspension liquid level was forcedly renewed by using a blower, to start to remove the solvent. In that course, after 15 minutes from the start of solvent removal, 75 parts of ammonia water diluted to 1% was added as an ionic substance. Subsequently, after 1 hour from the start of solvent removal, 25 parts of the like ammonia water was added. Further, after 2 hours from the start of solvent removal, 25 parts of the like ammonia water was added. Finally, after 3 hours from the start of solvent removal, 25 parts of the like ammonia water was added, thus 150 g of the dilute ammonia water was added in total. Further, keeping the temperature at 40° C., the system was held for 17 hours from the start of solvent removal. Thus, a toner fluid dispersion was obtained in which the solvent (ethyl acetate) was removed from suspended particles.

Washing and Dehydration Step:

To 300 parts of the toner fluid dispersion obtained in the solvent removal step, 80 parts of 10 mol/liter hydrochloric acid was added, followed by further addition of an aqueous 0.1 mol/liter sodium hydroxide solution to carry out neutralization treatment. Thereafter, washing with ion-exchanged water by suction filtration was repeated four times to obtain a toner cake. The toner cake thus obtained was dried by means of a vacuum dryer, followed by sifting through a 45-μm mesh sieve to obtain toner base particles.

Subsequent procedure in Toner Example 1 was repeated to produce a toner 17.

Comparative Toner Example 1

Production of Toner 18

A toner 18 for comparison was produced in the same way as Toner Example 1 except that the polymeric compound A was not used.

Comparative Toner Example 2

Production of Toner 19

A toner 19 for comparison was produced in the same way as Toner Example 1 except that a salicylic acid aluminum complex (BONTRON E-108, trade name; available from Orient Chemical Industries, Ltd.) was used in place of the polymeric compound A.

Comparative Toner Examples 3 & 4

Production of Toners 20 and 21

Toners 20 and 21 for comparison were produced in the same way as Toner Example 1 except that the polymeric compounds Q and R, respectively, were used in place of the polymeric compound A.

The measurement and evaluation of particle size distribution, charge quantity and reverse-polarity toner quantity of the toners produced as described above were made by the methods described previously. The results are shown in Table 3.

TABLE 3

Evaluation of Toner

| | Toner | Polymeric compound | Toner production process | Particle size distribution Av. particle diam.* (μm) | D4/D1 | Toner charge quantity Shaking 10 sec. | 300 sec. | Reverse = polarity toner quantity |
|---|---|---|---|---|---|---|---|---|
| | | | | Toner Example: | | | | |
| 1 | Toner 1 | Polymeric compound A | SusPoly | 6.8 | 1.22 | A | A | A |
| 2 | Toner 2 | Polymeric compound B | SusPoly | 7.1 | 1.30 | A | A | A |
| 3 | Toner 3 | Polymeric compound C | SusPoly | 7.2 | 1.25 | A | A | A |
| 4 | Toner 4 | Polymeric compound D | SusPoly | 7.6 | 1.27 | A | A | A |
| 5 | Toner 5 | Polymeric compound E | SusPoly | 6.9 | 1.28 | A | A | A |
| 6 | Toner 6 | Polymeric compound F | SusPoly | 6.7 | 1.27 | B | A | B |
| 7 | Toner 7 | Polymeric compound G | SusPoly | 6.8 | 1.30 | A | A | A |
| 8 | Toner 8 | Polymeric compound H | SusPoly | 7.3 | 1.29 | A | A | A |
| 9 | Toner 9 | Polymeric compound I | SusPoly | 7.8 | 1.26 | A | A | A |
| 10 | Toner 10 | Polymeric compound J | SusPoly | 7.5 | 1.25 | A | A | A |
| 11 | Toner 11 | Polymeric compound K | SusPoly | 6.6 | 1.27 | A | A | A |
| 12 | Toner 12 | Polymeric compound L | SusPoly | 6.8 | 1.28 | A | A | A |
| 13 | Toner 13 | Polymeric compound M | SusPoly | 7.4 | 1.27 | B | A | B |
| 14 | Toner 14 | Polymeric compound N | SusPoly | 7.1 | 1.30 | A | A | A |
| 15 | Toner 15 | Polymeric compound O | SusPoly | 7.0 | 1.26 | A | A | A |
| 16 | Toner 16 | Polymeric compound P | SusPoly | 6.8 | 1.27 | B | B | B |
| 17 | Toner 17 | Polymeric compound A | SusGran | 6.9 | 1.26 | A | A | A |
| | | | | Comparative Toner Example: | | | | |
| 1 | Toner 18 | none | SusPoly | 7.1 | 1.31 | D | D | D |
| 2 | Toner 19 | salicylic acid Al complex | SusPoly | 7.3 | 1.23 | B | B | C |
| 3 | Toner 20 | Polymeric compound Q | SusPoly | 7.4 | 1.25 | C | B | C |
| 4 | Toner 21 | Polymeric compound R | SusPoly | 7.0 | 1.28 | C | A | C |

SusPoly: suspension polymerization; SusGran: suspension granulation
*Weight-average particle diameter (D4)

As can be seen from Table 3, it has been ascertained that the toner of the present invention has a high charging rise speed, shows a high saturated charge quantity, and at the same time can keep any particles from forming which are of polarity reverse to the desired charge polarity.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-074834, filed Mar. 30, 2011, and No. 2011-074550, filed Mar. 30, 2011 which are hereby incorporated by reference herein in their entirety.

REFERENCE SIGNS LIST 11 conductive substrate
12 substrate holder stand
13 polymeric compound coating film
14 standard powder
15 standard powder feeder
16 standard powder receiver
17 electrometer
21 suction device
22 measuring container
23 conductive screen
24 lid
25 vacuum indicator
26 air-flow control valve
27 suction opening
28 capacitor
29 electrometer

The invention claimed is:

1. A polymerizable monomer, which is a compound selected from the group consisting of compounds represented by the following general formulas (2) to (4):

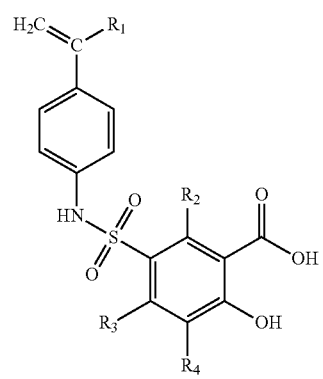

General formula (2)

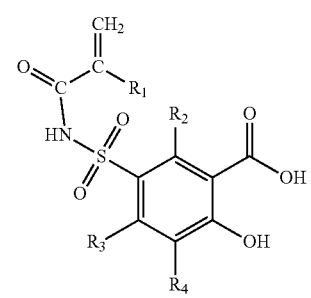

General formula (3)

-continued

General formula (4)

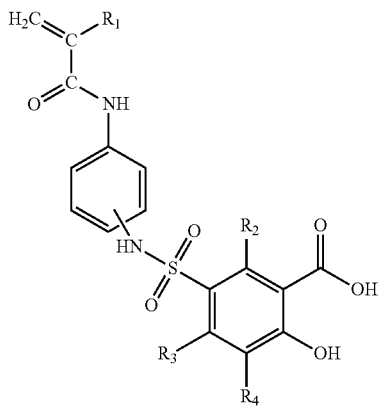

wherein $R_1$ represents a hydrogen atom or an alkyl group; $R_2$ to $R_4$ each represent a hydrogen atom, an alkyl group, an alkoxy group, a hydroxyl group or a halogen atom; and $R_3$ and $R_4$ may combine with each other to form a ring.

2. A polymeric compound containing at least one unit represented by the following general formula (5):

General formula (5)

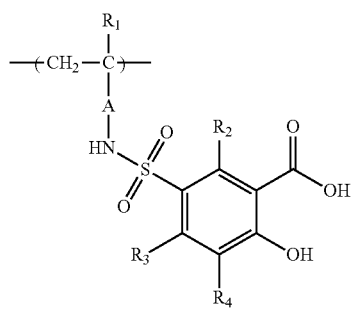

wherein $R_1$ represents a hydrogen atom or an alkyl group; $R_2$ to $R_4$ each represent a hydrogen atom, an alkyl group, an alkoxy group, a hydroxyl group or a halogen atom; $R_3$ and $R_4$ may combine with each other to form a ring; and A represents a divalent linking group.

3. The polymeric compound according to claim 2, which is a copolymer having the unit represented by the general formula (5) and at least one unit represented by the following general formula (6):

General formula (6)

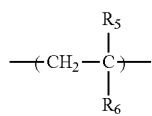

wherein $R_5$ represents a hydrogen atom or an alkyl group; and $R_6$ represents a phenyl group, a carboxyl group, a carboxylate group or a carboxylic acid amide group.

4. The polymeric compound according to claim 3, wherein $R_6$ represents a phenyl group or a carboxylate group.

5. The polymeric compound according claim 2, which has a weight-average molecular weight of from 3,000 to 100,000.

6. A charge control agent comprising the polymeric compound according to claim 2.

7. A developer bearing member comprising in an outermost surface layer thereof the charge control agent according to claim 6.

8. A toner comprising a binder resin, a colorant and the charge control agent according to claim 6.

9. The toner according to claim 8, which is produced by a suspension polymerization process.

10. The toner according to claim 8, which is produced by a suspension granulation process.

11. The polymeric compound according to claim 2, wherein the unit represented by the following general formula (5) is at least one unit selected from the group consisting of units represented by the following general formulas (A) to (C):

General formula (A)

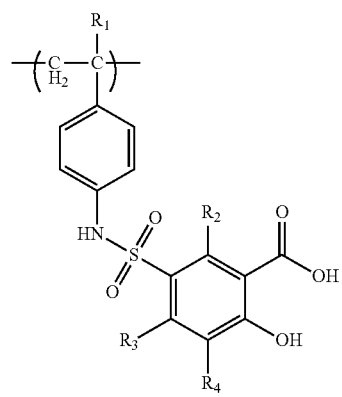

General formula (B)

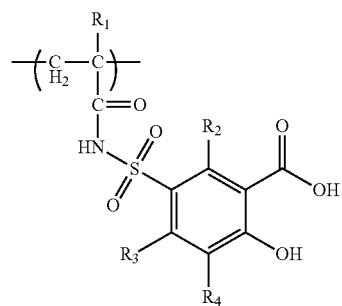

General formula (C)

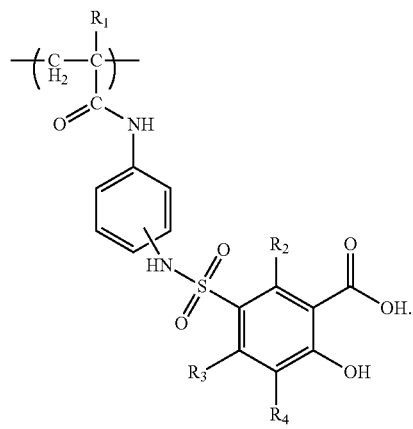

* * * * *